United States Patent
Muto et al.

(10) Patent No.: US 12,331,240 B2
(45) Date of Patent: Jun. 17, 2025

(54) ANTHRAQUINONE COMPOUND, LIQUID CRYSTAL COMPOSITION CONTAINING SAID COMPOUND, AND LIGHT-CONTROLLING ELEMENT

(71) Applicant: NIPPON KAYAKU KABUSHIKI KAISHA, Tokyo (JP)

(72) Inventors: Hitomi Muto, Tokyo (JP); Kohei Ohtani, Tokyo (JP); Yu Hattori, Tokyo (JP); Saori Suzuki, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/701,832

(22) PCT Filed: Nov. 4, 2022

(86) PCT No.: PCT/JP2022/041152
§ 371 (c)(1),
(2) Date: Apr. 16, 2024

(87) PCT Pub. No.: WO2023/080198
PCT Pub. Date: May 11, 2023

(65) Prior Publication Data
US 2024/0400899 A1   Dec. 5, 2024

(30) Foreign Application Priority Data
Nov. 4, 2021   (JP) .................. 2021-179925

(51) Int. Cl.
| G02F 1/1333 | (2006.01) |
| C09K 19/32 | (2006.01) |
| C09K 19/60 | (2006.01) |
| G02F 1/1334 | (2006.01) |

(52) U.S. Cl.
CPC ............ *C09K 19/322* (2013.01); *C09K 19/60* (2013.01); *G02F 1/1334* (2013.01)

(58) Field of Classification Search
CPC ...... C09K 19/12; C09K 19/60; C09K 19/603; C09K 19/322; C09K 2019/0448; G02F 1/1333; G02F 1/1334
See application file for complete search history.

(56) References Cited

U.S. PATENT DOCUMENTS

| 4,689,171 A | 8/1987 | Blunck et al. |
| 12,157,851 B2 * | 12/2024 | Ohtani .................. C09B 1/51 |
| 2018/0307077 A1 | 10/2018 | Miura et al. |

(Continued)

FOREIGN PATENT DOCUMENTS

| JP | 58-196260 A | 11/1983 |
| JP | 62-5941 A | 1/1987 |

(Continued)

OTHER PUBLICATIONS

International Search Report and Written Opinion mailed Jan. 24, 2023 in corresponding PCT application No. PCT/JP2022/041152.

*Primary Examiner* — Geraldina Visconti
(74) *Attorney, Agent, or Firm* — Nields, Lemack & Frame, LLC

(57) ABSTRACT

An anthraquinone compound represented by formula (1) (In the formula, $R_1$ and $R_4$ represent a hydrogen atom, a C1-12 alkyl group, a C1-12 alkoxy group, a halogen atom, $-CO_2R_9$, $-OCOR_9$, $-COR_9$, a cyano group, or a trifluoromethyl group. $R_2$, $R_3$, $R_5$, and $R_6$ represent a hydrogen atom, a C1-4 alkyl group, a C1-4 alkoxy group, a halogen atom, $-CO_2R_9$, $-OCOR_9$, $-COR_9$, a cyano group, or a trifluoromethyl group, $R_7$ and $R_8$ represent a hydrogen atom or a C1-8 alkyl group. $R_9$ represents a C1-12 alkyl group, a substituent represented by formula (a) (in the formula, $R_{10}$ represents a hydrogen atom, a C1-8 alkyl group, or a C1-8 alkoxy group), or a substituent represented by formula (b) (in the formula, $R_{11}$ represents a hydrogen atom or a C1-8 alkyl group)).

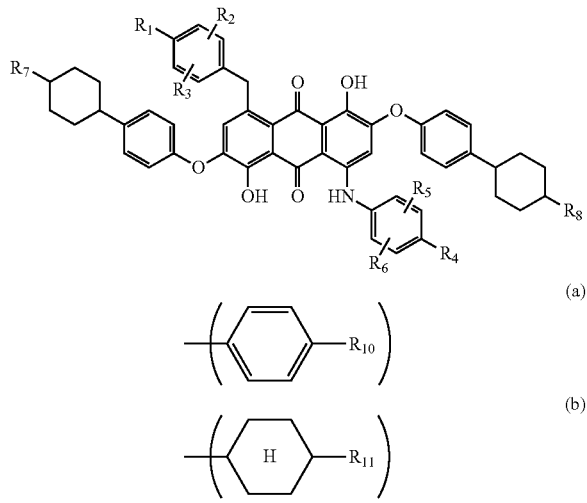

20 Claims, No Drawings

(56) References Cited

U.S. PATENT DOCUMENTS

| | | |
|---|---|---|
| 2024/0052243 A1 | 2/2024 | Ohtani et al. |
| 2024/0141234 A1* | 5/2024 | Muto ........................ C08F 2/50 |
| 2024/0400899 A1* | 12/2024 | Muto ..................... C09K 19/12 |
| 2024/0409497 A1* | 12/2024 | Ohtani .................. C07C 225/36 |

FOREIGN PATENT DOCUMENTS

| | | |
|---|---|---|
| JP | 63-501512 A1 | 6/1988 |
| JP | 3-47392 A | 2/1991 |
| JP | 4-264193 A | 9/1992 |
| JP | 2008-106107 A | 5/2008 |
| JP | 2011-190314 A | 9/2011 |
| JP | 2018-205746 A | 12/2018 |
| WO | 2022/138433 A1 | 6/2022 |

* cited by examiner

ANTHRAQUINONE COMPOUND, LIQUID CRYSTAL COMPOSITION CONTAINING SAID COMPOUND, AND LIGHT-CONTROLLING ELEMENT

TECHNICAL FIELD

The present invention relates to a novel anthraquinone compound, a liquid crystal composition containing the compound, and a light control element.

BACKGROUND ART

In vehicles such as trains and automobiles, and windows, doors, partitions, and the like of buildings such as business buildings and hospitals, various devices related to light control films for controlling transmission of external light have been proposed for the purpose of protecting privacy and the like (see Patent Literatures 1 and 2). Examples of such light control films include ones utilizing a liquid crystal. Usually, the liquid crystal light control film can block a field of view by controlling transmission and scattering of light depending on whether or not a voltage is applied, but cannot block light itself, and therefore glare tends to increase due to light scattering. Therefore, for the purposes of reducing glare, improving contrast, and the like, attempts have been made to use a dye as a material of a light control panel (see Patent Literatures 3 and 4). For example, in the case of using such a light control panel for a window glass of an automobile, from the viewpoints of practicality and designability, there is an increasing demand for a black element capable of blocking visible light, in addition to having good visibility without fogging or a color residue at the time of transparency. There is a strong demand for light resistance and heat tolerance during current supply with a small color change both at the time of applying no voltage and at the time of applying a voltage when exposed to light or voltage for a long period of time at high temperatures in outdoor use.

Dichroic dyes have been commonly known as the dyes to be used in liquid crystal light control films. As a light control element using a liquid crystal composition containing a dichroic dye, GH (guest-host) type has been known, and various dichroic dyes have been proposed (see Patent Literature 5).

Such dichroic dyes are required to have light resistance, UV resistance, heat resistance, compatibility (solubility) with constituent components of the liquid crystal composition, and the like, in addition to contrast or dichroic ratio when used in a display element, and efforts have been made to improve these characteristics. On the other hand, the light shielding property in the case of a black light control element is a problem. A black light control element containing dyes is generally produced by mixing yellow, red, and blue dyes and using the resultant mixture. The black light control element desirably absorbs light in a wide wavelength range at the time of opacity from the viewpoints of practicality and designability, and it is important to control transmission of light particularly in a long wavelength region of 650 nm or more in order to suppress light leakage. For example, the blue dichroic dye described in Patent Literature 5 does not satisfy market requirements for a black light control element exhibiting high light shielding property because a maximum absorption wavelength ($\lambda$max) is on the short wavelength side, as shown in Comparative Examples of the present specification. Even though the blue dichroic dye described in Patent Literature 6 has an absorption peak in a long wavelength region, the blue dichroic dye has a low contrast and thus is poor in practicality. Therefore, a dichroic dye satisfying both of these properties is strongly required.

CITATION LIST

Patent Literatures

PATENT LITERATURE 1: JPS63-501512A
PATENT LITERATURE 2: JPH03-47392A
PATENT LITERATURE 3: JP2018-205746A
PATENT LITERATURE 4: JP2011-190314A
PATENT LITERATURE 5: JPS62-5941A
PATENT LITERATURE 6: JPH04-264193A

SUMMARY OF INVENTION

Technical Problem

A first object of the present invention is to provide a novel anthraquinone compound having a maximum absorption wavelength in a long wavelength region of 650 nm or more and excellent spectral characteristics.

Another object of the present invention is to provide this novel anthraquinone compound, a liquid crystal composition containing the compound, and a light control element excellent in contrast containing the liquid crystal composition or a cured product of the liquid crystal composition.

Solution to Problem

The present inventors have succeeded in obtaining a novel anthraquinone compound having a specific structure and having a maximum absorption wavelength in a long wavelength region of 650 nm or more.

The present inventors have also found that a light control element excellent in contrast can be obtained by using this novel anthraquinone compound.

That is, aspects or embodiments encompassed within the scope of the present invention are as follows.

[1]. An anthraquinone compound represented by the following formula (1):

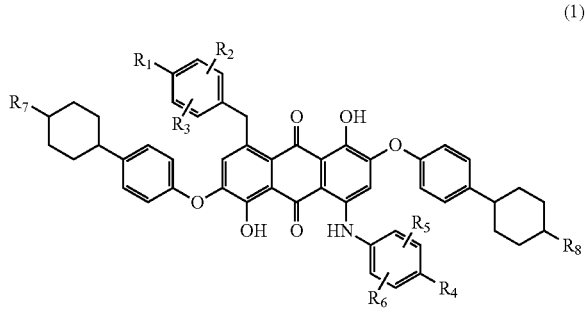

(1)

wherein $R_1$ and $R_4$ each independently represent a hydrogen atom, a C1-C12 linear or branched alkyl group, a C1-C12 linear or branched alkoxy group, a halogen atom, —$CO_2R_9$, —$OCOR_9$, —$COR_9$, a cyano group, or a trifluoromethyl group, $R_2$, $R_3$, $R_5$, and $R_6$ each independently represent a hydrogen atom, a C1-C4 linear or branched alkyl group, a C1-C4 linear or branched alkoxy group, a halogen atom, —$CO_2R_9$, —$OCOR_9$, —$COR_9$, a cyano group, or a trifluoromethyl group. $R_7$ and $R_8$ each independently represent a hydrogen atom or a C1-C8 linear or branched alkyl group, and $R_9$ each independently represents a C1-C12 linear or branched alkyl group, a substituent represented by the following formula (a):

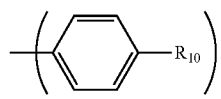

(wherein $R_{10}$ represents a hydrogen atom, a C1-C8 linear or branched alkyl group, or a C1-C8 linear or branched alkoxy group), or a substituent represented by the following formula (b):

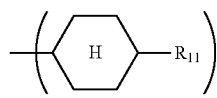

(wherein $R_1$ represents a hydrogen atom or a C1-C8 linear or branched alkyl group).

[2]. The anthraquinone compound according to the above item [1] wherein at least one of $R_1$ to $R_6$ is other than a hydrogen atom.

[3]. The anthraquinone compound according to the above item [1] or [2], wherein $R_9$ is each independently a C1-C8 linear or branched alkyl group.

[4]. The anthraquinone compound according to any one of the above items [1] to [3], wherein $R_1$ and $R_4$ are each independently a hydrogen atom, a C1-C8 linear or branched alkyl group, a C1-C8 linear or branched alkoxy group, a fluorine atom, a chlorine atom, —$CO_2R_9$, —$COR_9$, a cyano group, or a trifluoromethyl group, and $R_2$, $R_3$, $R_5$, and $R_6$ are each independently a hydrogen atom, a C1-C4 linear alkyl group, a C1-C4 linear alkoxy group, a fluorine atom, a chlorine atom, —$CO_2R_9$, —$COR_9$, a cyano group, or a trifluoromethyl group.

[5. The anthraquinone compound according to any one of the above items 1] to [4], wherein at least one of $R_1$, $R_2$, $R_4$, and $R_5$ is a fluorine atom, a chlorine atom, —$CO_2R_9$, —$COR_9$, a cyano group, or a trifluoromethyl group.

[6]. The anthraquinone compound according to the above item [5], wherein at least one of $R_1$, $R_2$, $R_4$, and $R_5$ is a fluorine atom, —$CO_2R_9$, or a cyano group.

[7]. The anthraquinone compound according to any one of the above items [1] to [6], wherein $R_3$ and $R_6$ are a hydrogen atom.

[8]. The anthraquinone compound according to any one of the above items [1] to [7], wherein only one of $R_1$ and $R_2$ is a hydrogen atom, and only one of $R_4$ and $R_5$ is a hydrogen atom.

[9]. The anthraquinone compound according to any one of the above items [1] to [8], wherein $R_2$ and $R_5$ are a by hydrogen atom.

[10]. The anthraquinone compound according to any one of the above items [1] to [9], wherein $R_4$ is a C3-C8 linear or branched alkyl group.

[11]. The anthraquinone compound according to any one of the above items [1] to [10], wherein $R_7$ and $R_8$ are each independently a C3-C8 linear alkyl group.

[12]. The anthraquinone compound according to any one of the above items [1] to [11], wherein a maximum absorption wavelength is 650 nm or more.

[13]. A liquid crystal composition comprising the anthraquinone compound according to any one of the above items [1] to [12] and a liquid crystal material.

[14]. The liquid crystal composition according to the above item [13], comprising a photocurable compound and a photopolymerization initiator.

[15]. The liquid crystal composition according to the above item [13] or [14], comprising a dye compound other than the anthraquinone compound represented by formula (1).

[16]. A photocured product of the liquid crystal composition according to the above item [14] or [15].

[17]. A light control element comprising the liquid crystal composition according to any one of the above items [13] to [15] or the photocured product according to the above item [16] sandwiched between a pair of substrates disposed opposite to each other, at least one of which is a transparent substrate having a transparent electrode.

[18]. The light control element according to the above item [17], wherein both of the pair of substrates are transparent substrates having a transparent electrode.

Advantageous Effects of Invention

By using the anthraquinone compound of the present invention as a dichroic dye for a liquid crystal light control element, it is possible to obtain a light control element in which light leakage at the time of light shielding can be suppressed and which is excellent in contrast.

DESCRIPTION OF EMBODIMENTS

Hereinafter, the present invention will be described in detail.

An anthraquinone compound of the present invention is represented by the following formula (1)

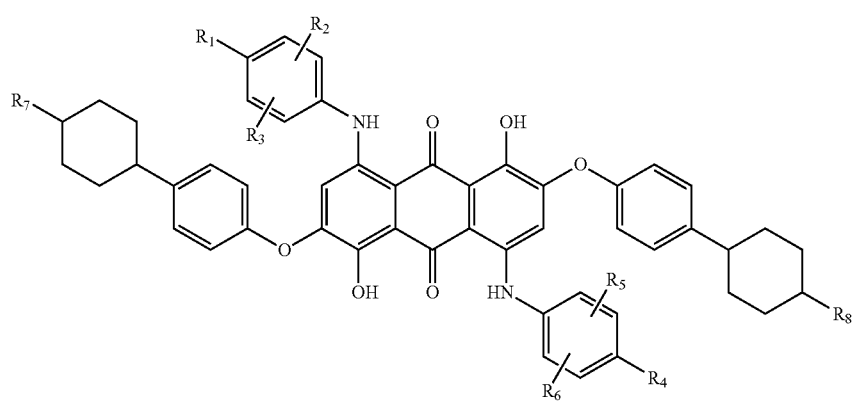

In formula (1) $R_1$ and $R_4$ each independently represent a hydrogen atom, a C1-C12 linear or branched alkyl group, a C1-C12 linear or branched alkoxy group, a halogen atom, a —$CO_2R_9$ group, a —$OCOR_9$ group, a —$COR_9$ group, a cyano group, or a trifluoromethyl group. $R_2$, $R_3$, $R_5$, and $R_6$ each independently represent a hydrogen atom, a C1-C4 linear or branched alkyl group, a C1-C4 linear or branched alkoxy group, a halogen atom, —$CO_2R_9$, —$OCOR_9$, —$COR_9$, a cyano group, or a trifluoromethyl group. $R_7$ and $R_8$ each independently represent a hydrogen atom or a C1-C8 linear or branched alkyl group.

The C1-C12 alkyl group represented by $R_1$ and $R_4$ in formula (1) may be linear or branched. Specific examples thereof include a methyl group, an ethyl group, a n-propyl group, an iso-propyl group, a r-butyl group, an iso-butyl group, a sec-butyl group, a t-butyl group, a n-pentyl group, an iso-pentyl group, a neo-pentyl group, a t-pentyl group, a hexyl group, a heptyl group, an octyl group, a nonyl group, a decyl group, an undecyl group, a dodecyl group, a 2-ethylhexyl group, a 2-propylhexyl group, a 2-butylhexyl group, a 2-pentylhexyl group, and a 2-pentylheptyl group. Among them, a C1-C8 linear or branched alky group is preferable, a C3-C8 linear or branched alkyl group is more preferable, and a C3-C8 linear alkyl group is still more preferable.

The C1-C12 alkoxy group represented by $R_1$ and $R_4$ in formula (1) may be linear or branched. Specific examples thereof include a methoxy group, an ethoxy group, a n-propoxy group, an iso-propoxy group, a n-butoxy group, an iso-butoxy group, a sec-butoxy group, a t-butoxy group, a n-pentyloxy group, an iso-pentyloxy group, a neo-pentyloxy group, a t-pentyloxy group, a hexyloxy group, a heptyloxy group, an octyloxy group, a nonyloxy group, a decyloxy group, an undecyloxyl group, a dodecyloxy group, a 2-ethylhexyloxy group, a 2-propylhexyloxy group, a 2-butylhexyloxy group, a 2-pentylhexyloxy group, and a 2-pentylheptyloxy group. Among them, a C1-C8 linear or branched alkoxy group is preferable.

Specific examples of the halogen atom represented by $R_1$ and $R_4$ in formula (1) include a fluorine atom, a chlorine atom, a bromine atom, and an iodine atom. A chlorine atom or a fluorine atom is preferable, and a fluorine atom is more preferable.

$R_9$ in —$CO_2R_9$, —$OCOR_9$, and —$COR_9$ which are options of $R_1$ and $R_4$ in formula (1) represents a C1-C12 linear or branched alkyl group, a substituent represented by the following formula (a), or a substituent represented by the following formula. (b). When two or more $R_9$'s are present in formula (1), $R_9$'s may be the same or different.

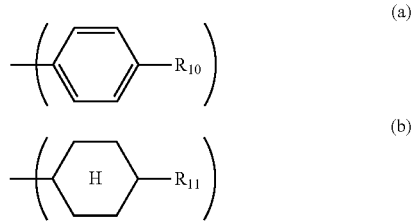

In formula (a), $R_{10}$ represents a hydrogen atom, a C1-C8 linear or branched alkyl group, or a C1-C8 linear or branched alkoxy group.

In formula (b), $R_{11}$ represents a hydrogen atom or a C1-C8 linear or branched alkyl group.

The C1-C12 alkyl group represented by $R_9$ may be linear or branched. Specific examples thereof include a methyl group, an ethyl group, a n-propyl group, an iso-propyl group, a n-butyl group, an iso-butyl group, a sec-butyl group, a t-butyl group, a n-pentyl group, an iso-pentyl group, a neo-pentyl group, a t-pentyl group, a hexyl group, a heptyl group, an octyl group, a nonyl group, a decyl group, an undecyl group, a dodecyl group, a 2-ethylhexyl group, a 2-propylhexyl group, a 2-butylhexyl group, a 2-pentylhexyl group, and a 2-pentylheptyl group. Among them, a C1-C8 linear or branched alkyl group is preferable, a C1-C4 linear or branched alkyl group is more preferable, and a C1-C4 linear alkyl group is still more preferable.

The C1-C8 alkyl group represented by $R_{10}$ and $R_{11}$ in formula (a) and formula (b) may be linear or branched. Specific examples thereof include a methyl group, an ethyl group, a n-propyl group, an iso-propyl group, a n-butyl group, an iso-butyl group, a sec-butyl group, a t-butyl group, a n-pentyl group, an iso-pentyl group, a neo-pentyl group, a t-pentyl group, a hexyl group, a heptyl group, an octyl group, and a 2-ethylhexyl group. Among them, a C4-C8 linear or branched alkyl group is preferable, and a C4-C8 linear alkyl group is more preferable.

The C1-C8 alkoxy group represented by $R_{10}$ in formula (a) may be linear or branched. Specific examples thereof include a methoxy group, an ethoxy group, a n-propoxy group, an iso-propoxy group, a n-butoxy group, an iso-butoxy group, a sec-butoxy group, a t-butoxy group, a n-pentyloxy group, an iso-pentyloxy group, a neo-pentyloxy group, a t-pentyloxy group, a hexyloxy group, a heptyloxy group, an octyloxy group, and a 2-ethylhexyloxy group. Among them, a C4-C8 linear or branched alkoxy group is preferable, and a C4-C8 linear alkoxy group is more preferable.

$R_1$ and $R_4$ in formula (1) are each independently preferably a C1-C12 linear or branched alkyl group, a C1-C12 linear or branched alkoxy group, a fluorine atom, a chlorine atom, —$CO_2R_9$, —$COR_9$, a cyano group, or a trifluoromethyl group. $R_1$ and $R_4$ in formula (1) are each independently more preferably a C1-C8 linear or branched alkyl group, a C1-C8 linear or branched alkoxy group, a fluorine atom, a chlorine atom, —$CO_2R_9$, —$COR_9$, a cyano group, or a trifluoromethyl group. $R_1$ and $R_4$ in formula (1) are each independently still more preferably a C1-C8 linear or branched alkyl group, a C1-C8 linear or branched alkoxy group, a fluorine atom, —$CO_2R_9$, or a cyano group. $R_4$ in formula (1) is particularly preferably a C3-C8 linear or branched alkyl group.

The C1-C4 alkyl group represented by $R_2$, $R_3$, $R_5$, and $R_6$ in formula (1) may be linear or branched. Specific examples thereof include a methyl group, an ethyl group, a n-propyl group, an iso-propyl group, a n-butyl group, an iso-butyl group, a sec-butyl group, and a t-butyl group. A methyl group or an ethyl group is preferable.

The C1-C4 alkoxy group represented by $R_2$, $R_3$, $R_5$, and $R_6$ in formula (1) may be linear or branched. Specific examples thereof include a methoxy group, an ethoxy group, a n-propoxy group, an iso-propoxy group, a n-butoxy group, an iso-butoxy group, a sec-butoxy group, and a t-butoxy group. A methoxy group or an ethoxy group is preferable.

Specific examples of the halogen atom represented by $R_2$, $R_3$, $R_5$, and $R_6$ in formula (1) include a fluorine atom, a chlorine atom, a bromine atom, and an iodine atom. Among them, a chlorine atom or a fluorine atom is preferable, and a fluorine atom is more preferable.

$R_9$ in —$CO_2R_9$, —$OCOR_9$, and —$COR_9$ which are options of $R_2$, $R_3$, $R_5$, and $R_6$ in formula (1) has the same meaning as $R_9$ in —$CO_2R_9$, —$OCOR_9$, and —$COR_9$ which are options of $R_1$ and $R_4$. Preferred examples of $R_9$ in —CO₂R₉, —OCOR₉, and —COR₉ which are options of R₂, R₃, R₅, and R₆ are the same as preferred examples of R₉ in —CO₂R₉, —OCOR₉, and —COR₉ which are options of R₁ and R₄.

R₂, R₃, R₅, and R₆ in formula (1) are each independently preferably a hydrogen atom, a C1-C4 linear or branched alkyl group, a C1-C4 linear or branched alkoxy group, a fluorine atom, a chlorine atom, —CO₂R₉, —COR₉, a cyano group, or a trifluoromethyl group. As R₂, R₃, R₅, and R₆ in formula (1), it is more preferable that R₂ and R₅ are each independently a hydrogen atom, a C1-C4 linear alkyl group, a C1-C4 linear alkoxy group, a fluorine atom, a chlorine atom, —CO₂R₉, —COR₉, a cyano group, or a trifluoromethyl group, and R₃ and R₆ are a hydrogen atom. As R₂, R₃, R₅, and R₆ in formula (1), it is still more preferable that R₂ and R₅ are each independently a hydrogen atom, a C1-C4 linear alkyl group, a fluorine atom, —CO₂R₉, or a cyano group, and R₃ and R₆ are a hydrogen atom.

In formula (I), it is preferable that the number of substituents other than the hydrogen atom of the phenyl group having R₁, and the number of substituents other than the hydrogen atom of the phenyl group having R₄ are each independently 0 to 2, that is, at least one of R₁ to R₃ is a hydrogen atom and at least one of R₄ to R₆ is a hydrogen atom. It is more preferable that the number of substituents of at least one of these phenyl groups is 0 or 1, that is, at least two of R₁ to R₃ are a hydrogen atom, and/or at least two of R₄ to R₆ are a hydrogen atom. It is still more preferable that the number of substituents of both of these phenyl groups is 0 or 1, that is, at least two of R₁ to R₃ are a hydrogen atom, and at least two of R₄ to R₆ are a hydrogen atom.

In formula (1), the positions of the substituents other than the hydrogen atom on the phenyl group having R₁ and the phenyl group having R₄ are each independently preferably the 2-position alone, the 3-position alone, the 4-position alone, the 2-position and the 4-position, or the 3-position and the 4-position, more preferably the 2-position alone, the 3-position alone, or the 4-position alone, and still more preferably the 2-position alone or the 4-position alone, when described with the numbers shown in the following formula (3).

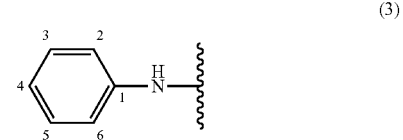 [SMILES: *Nc1ccccc1]

(3)

In formula (1), at least one of R₁, R₂, R₄, and R₅ is preferably a fluorine atom, a chlorine atom, —CO₂R₉, —COR₉, a cyano group, or a trifluoromethyl group, and at least one thereof is more preferably a fluorine atom, —CO₂R₉, or a cyano group.

The C1-C8 alkyl group represented by R₇ and R₈ in formula (1) may be linear or branched. Specific examples thereof include a methyl group, an ethyl group, a n-propyl group, an iso-propyl group, a n-butyl group, an iso-butyl group, a sec-butyl group, a t-butyl group, a n-pentyl group, an iso-pentyl group, a neo-pentyl group, a t-pentyl group, a hexyl group, a heptyl group, an octyl group, and a 2-ethylhexyl group. Among them, a C3-C8 linear alkyl group is preferable.

Preferable specific examples of the compound represented by formula (1) include the following compounds, but the present invention is not limited thereto. In the structural formulas described in the present specification, all alkyl groups represented only by the number of carbon atoms and the number of hydrogen atoms and having a non-limiting structure are linear alkyl groups.

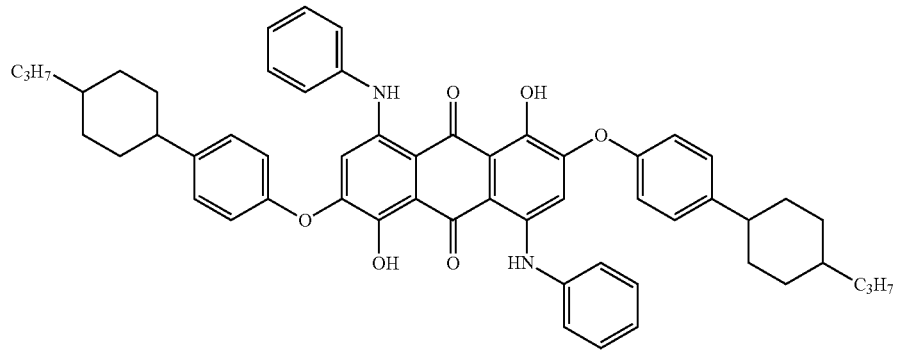

No.1

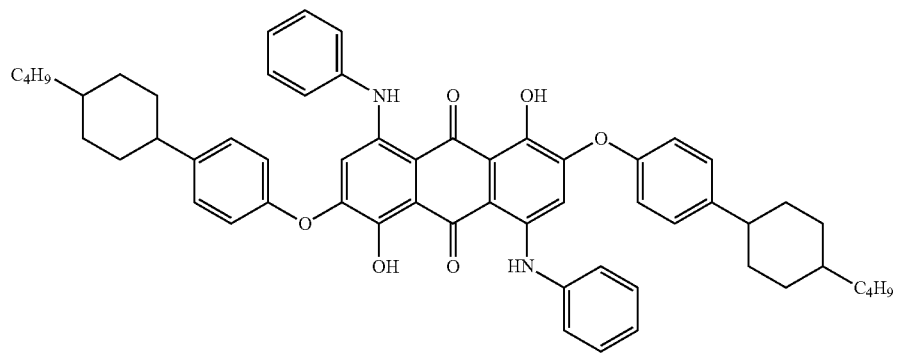

No.2

-continued
No.3
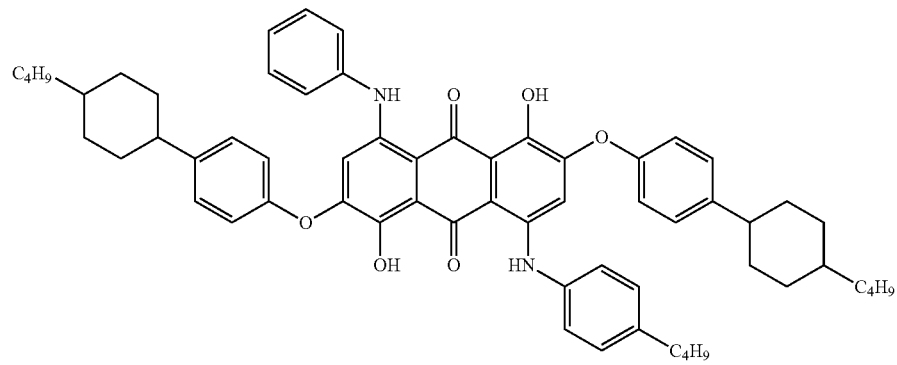
No.4
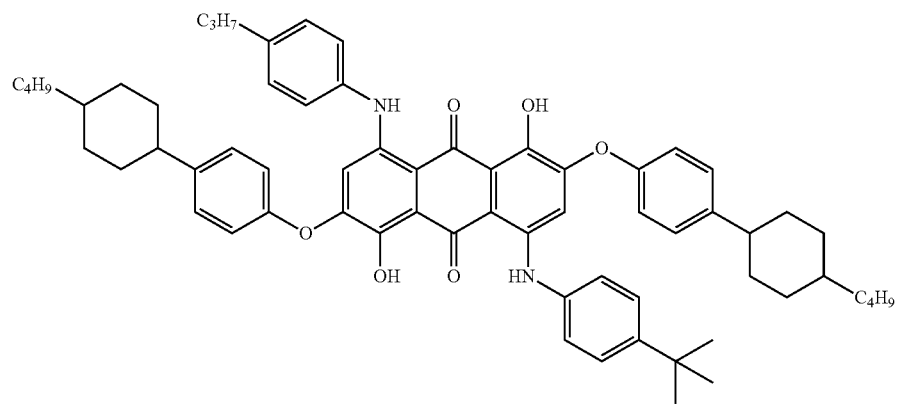
No.5
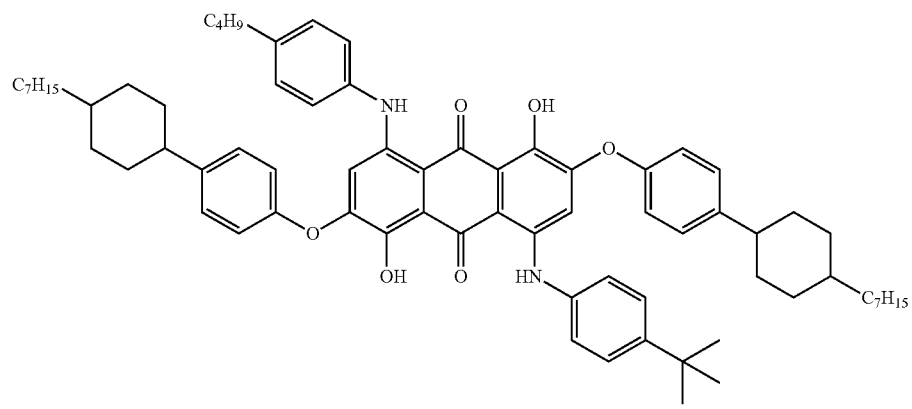
No.6
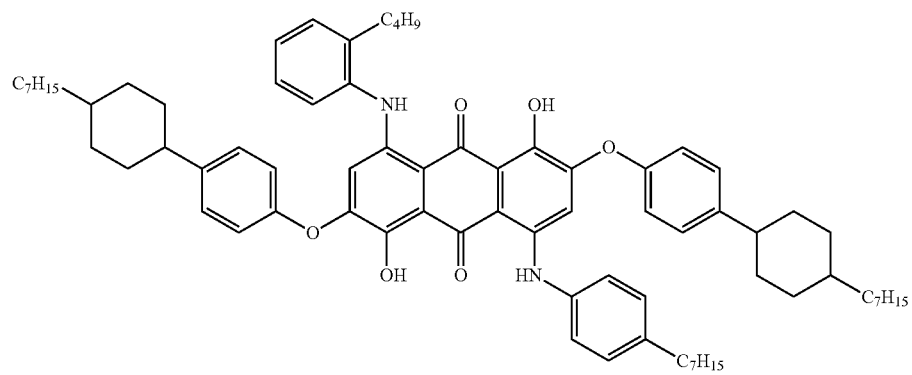

No.7
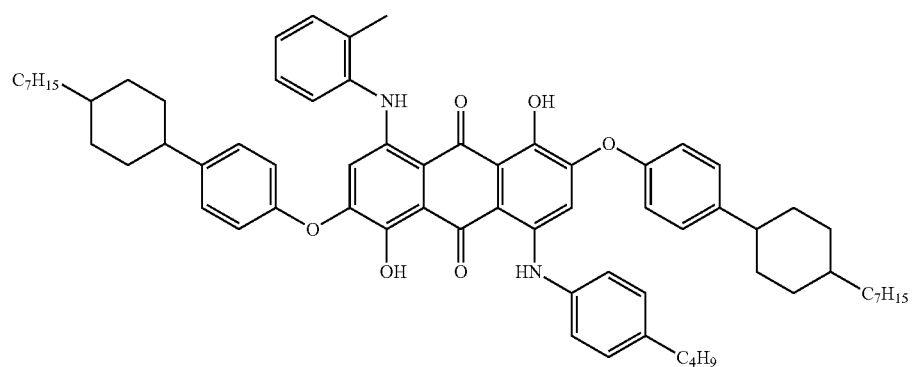
No.8
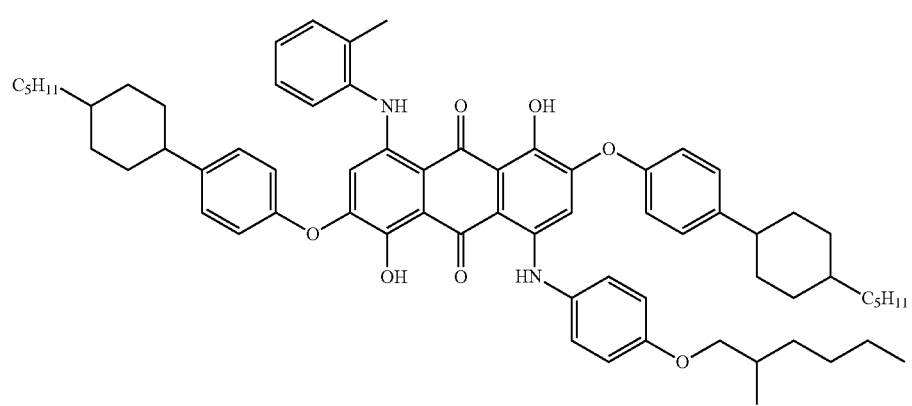
No.9
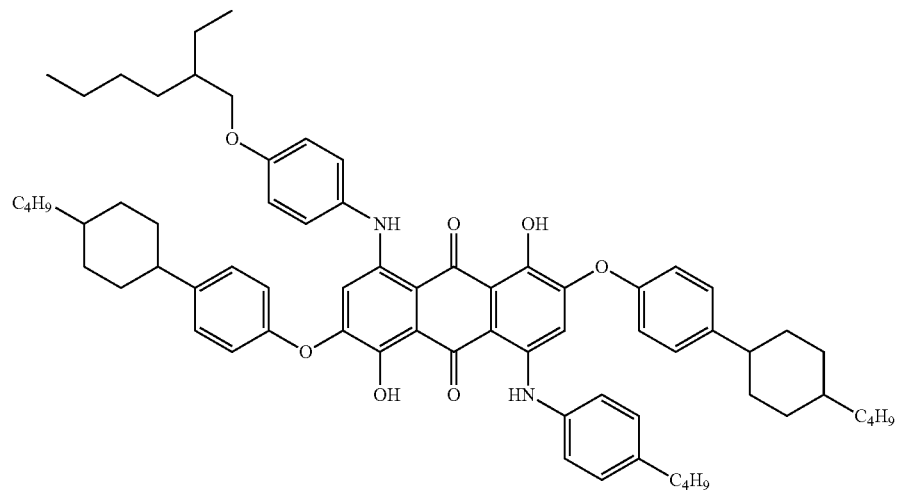
No.10
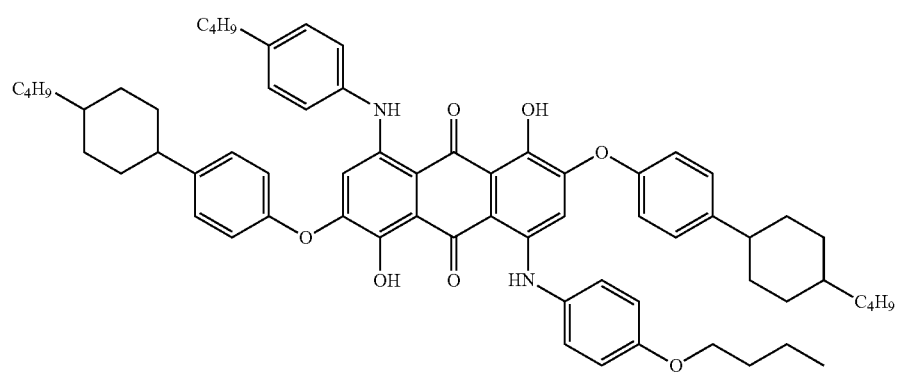

-continued
No.11
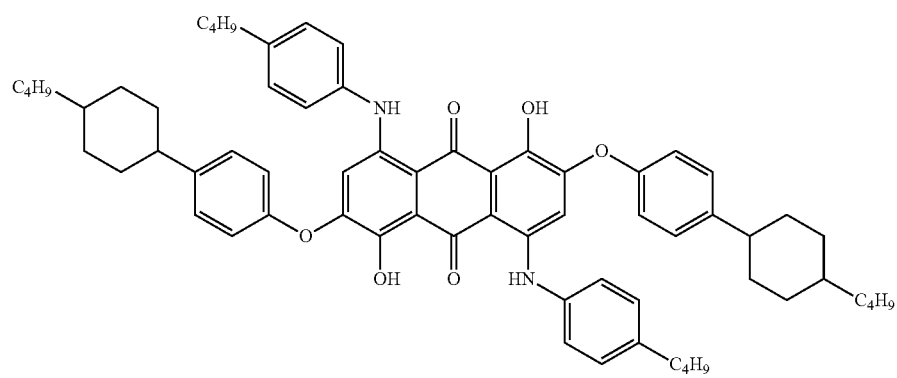
No.12
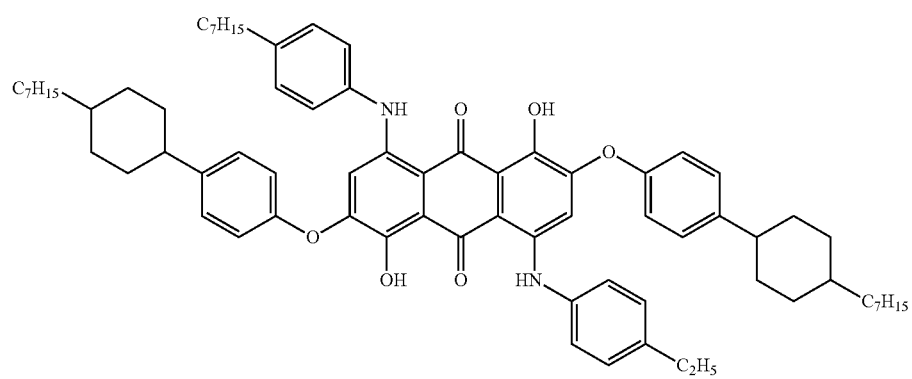
No.13
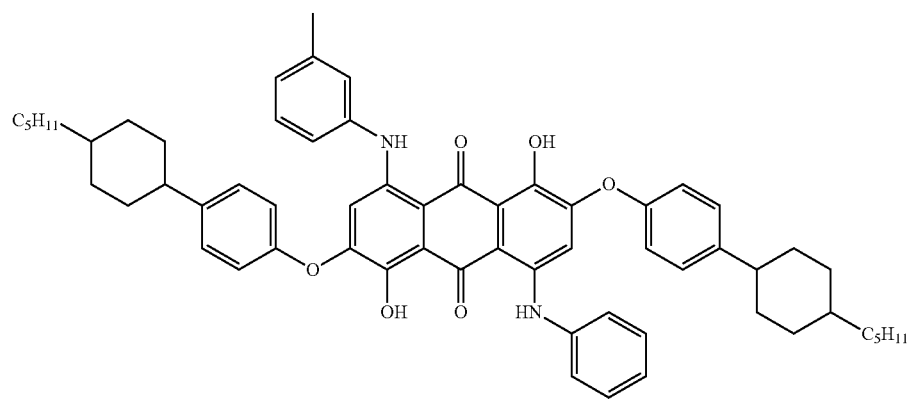
No.14
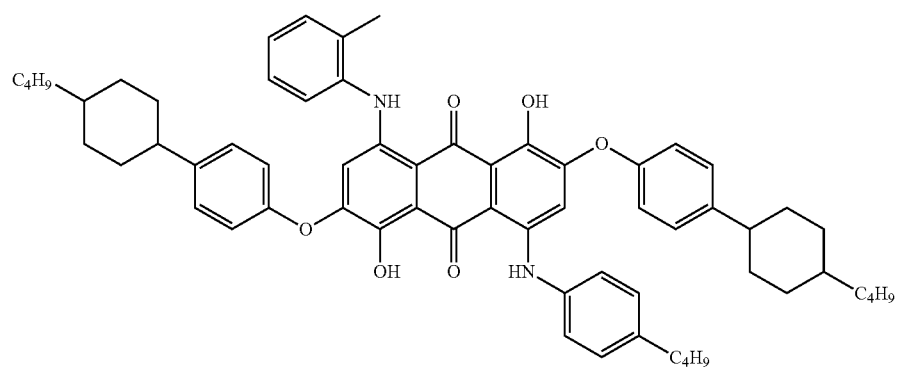

-continued
No.15
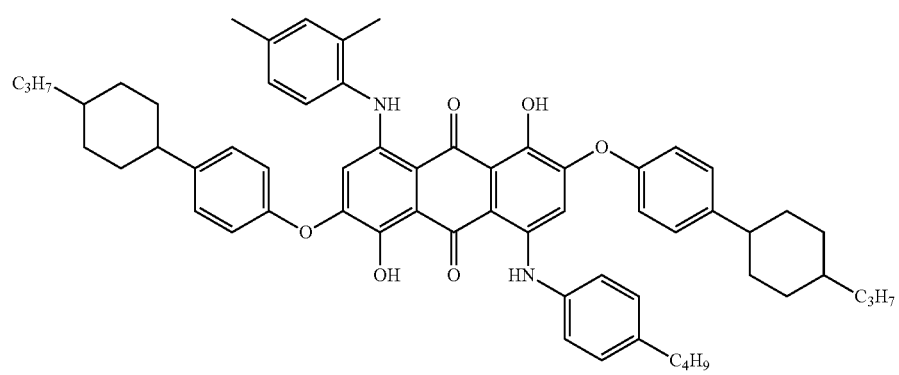
No.16
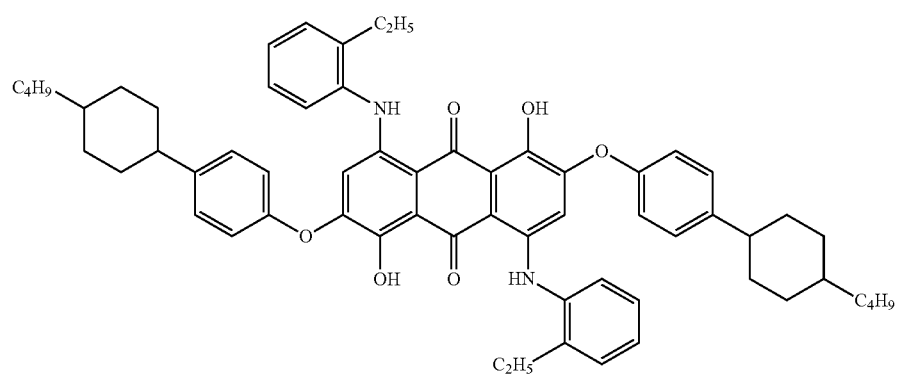
No.17
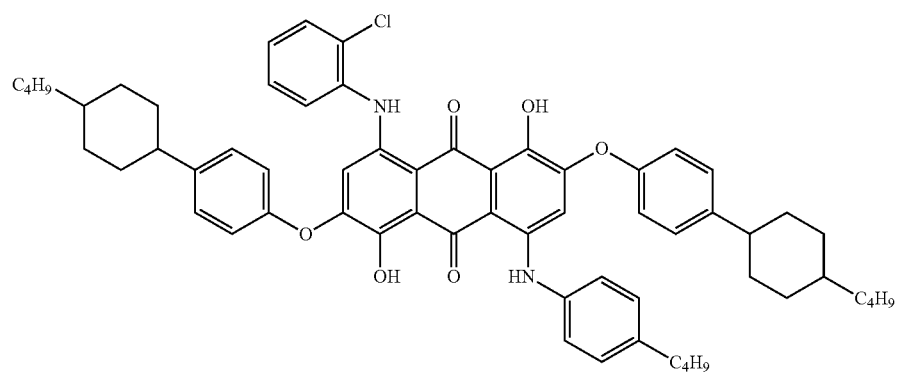
No.18
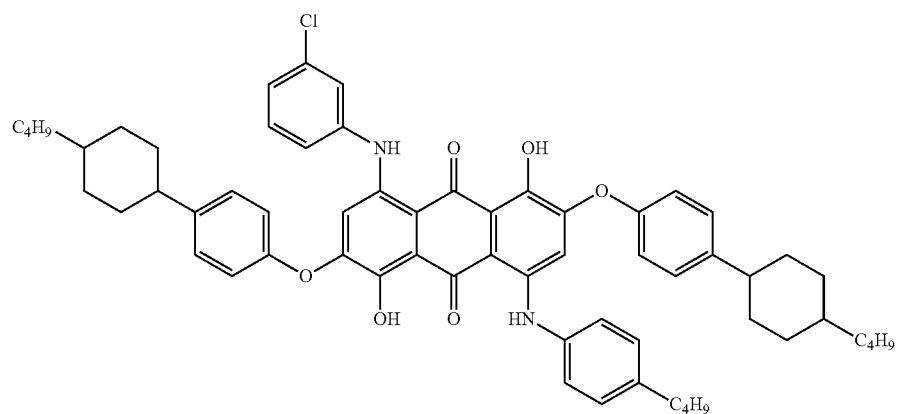

-continued
No.19
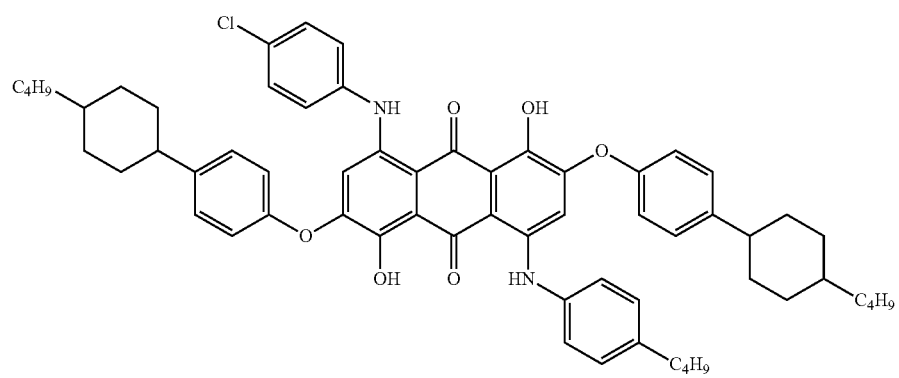
No.20
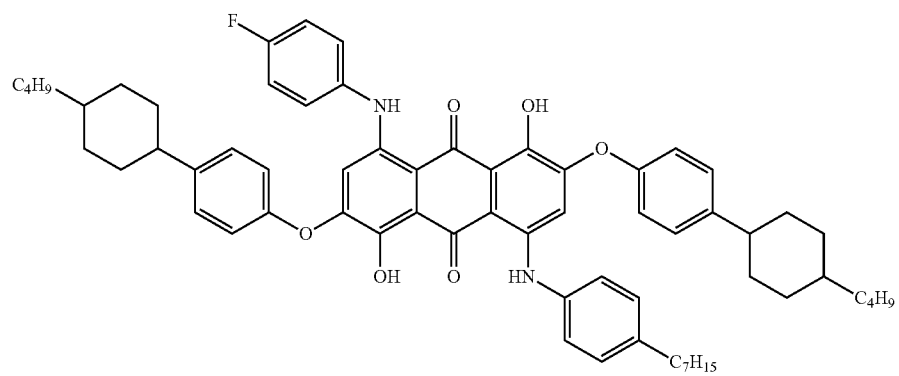
No.21
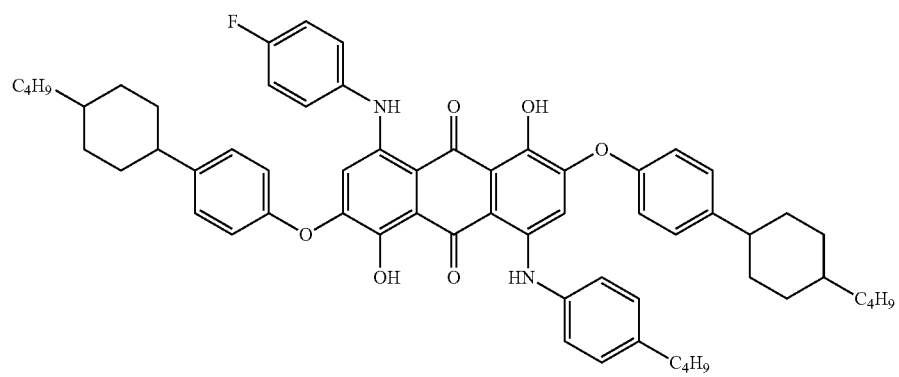
No.22
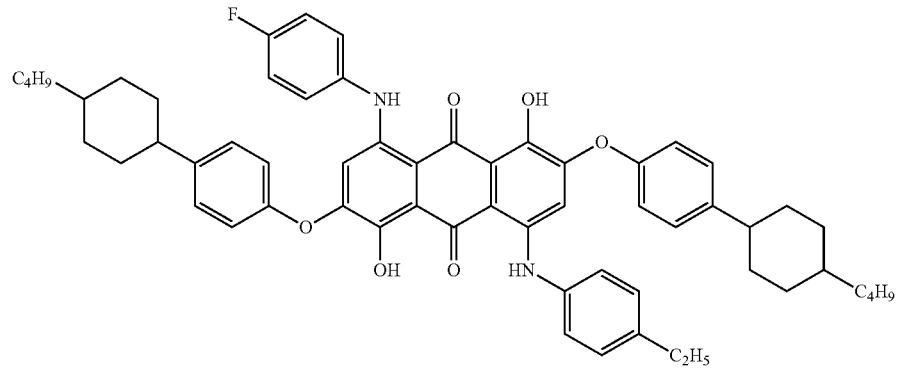

-continued
No.23
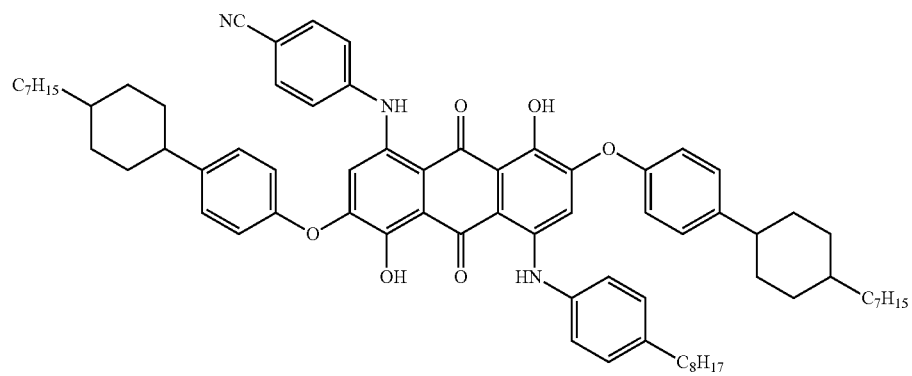
No.24
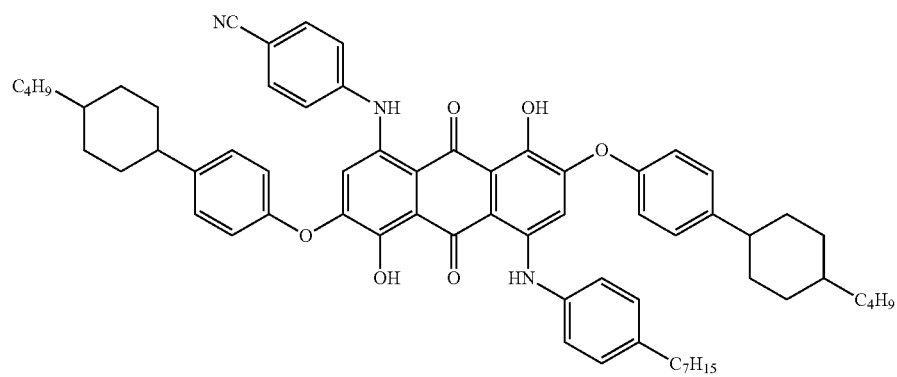
No.25
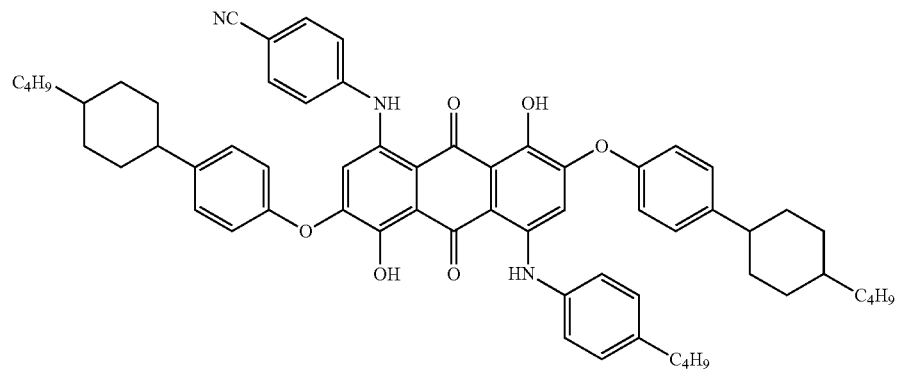
No.26
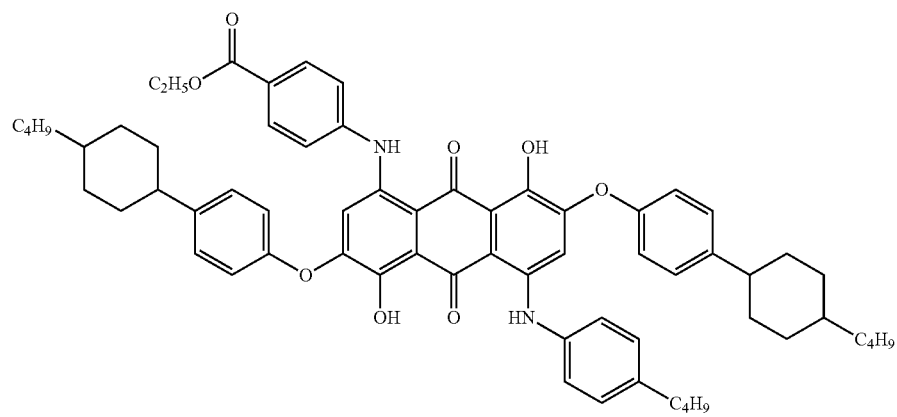

-continued
No.27
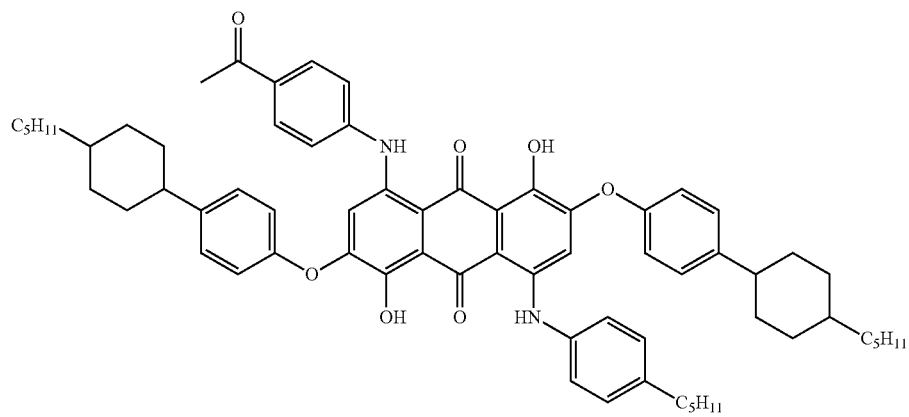
No.28
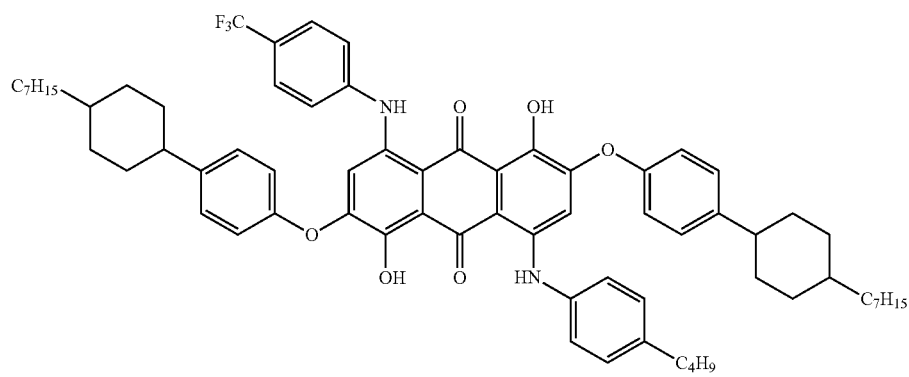
No.29
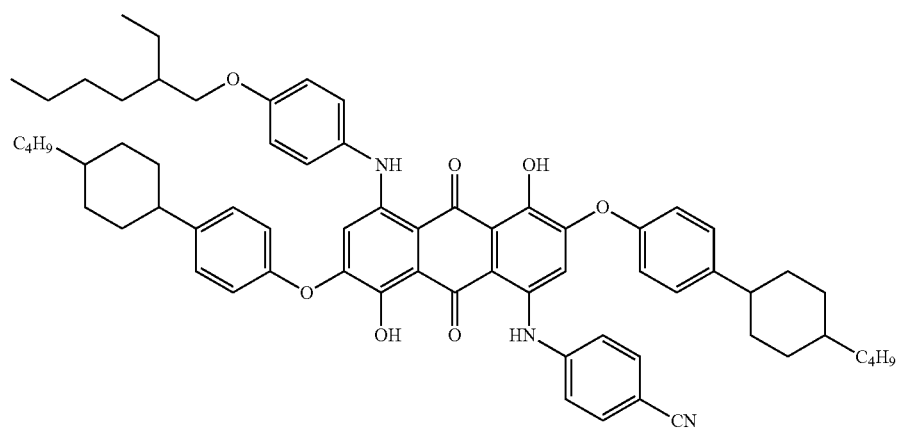
No.30
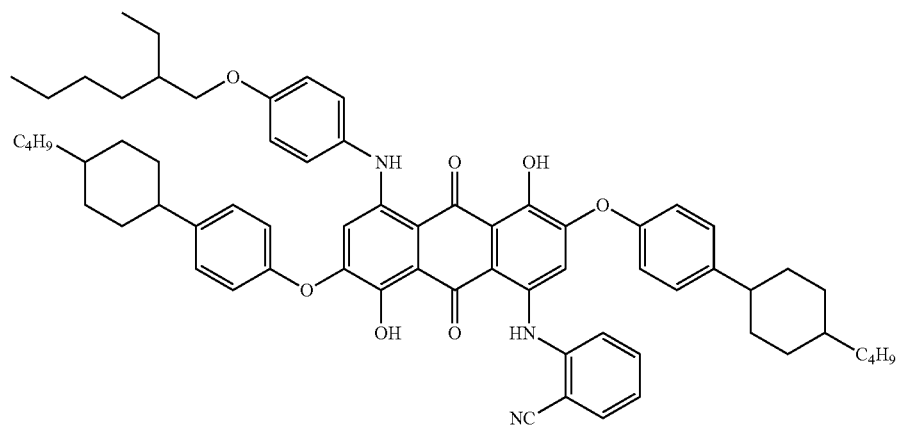

No.31
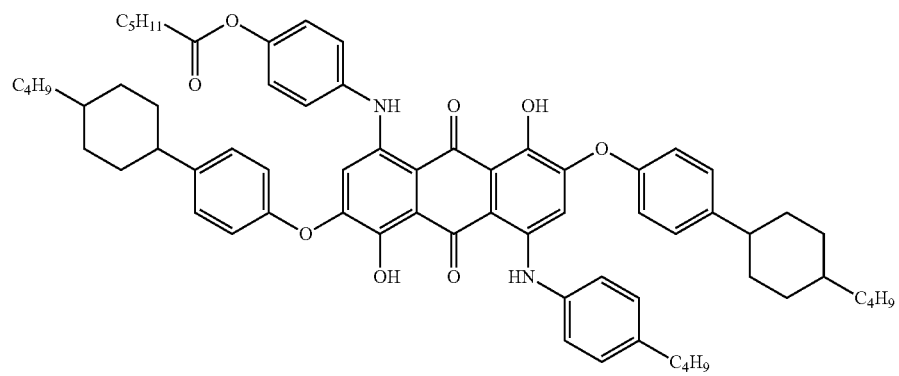
No.32
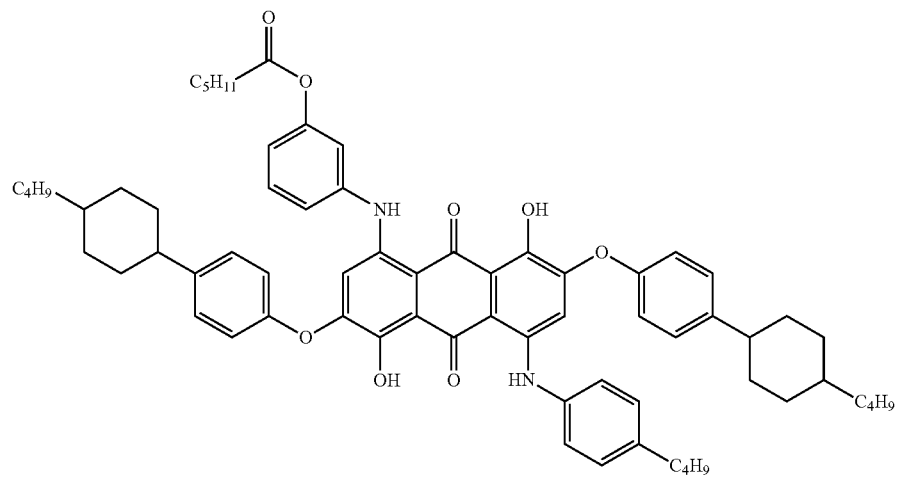
No.33
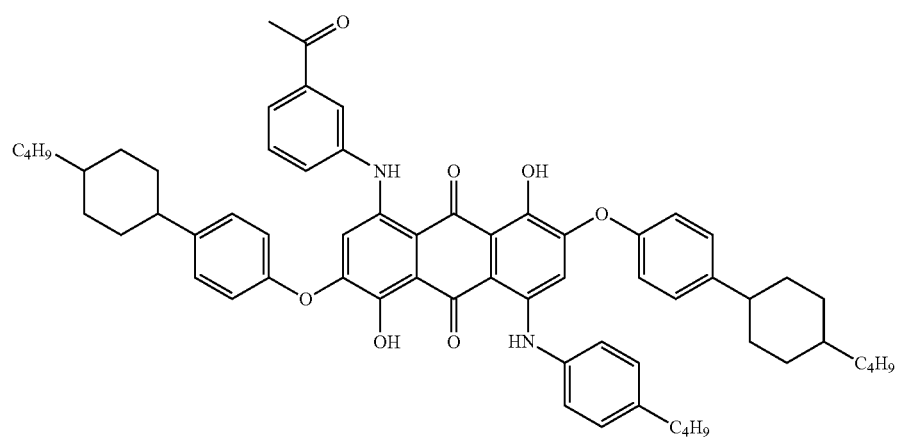

-continued
No.34
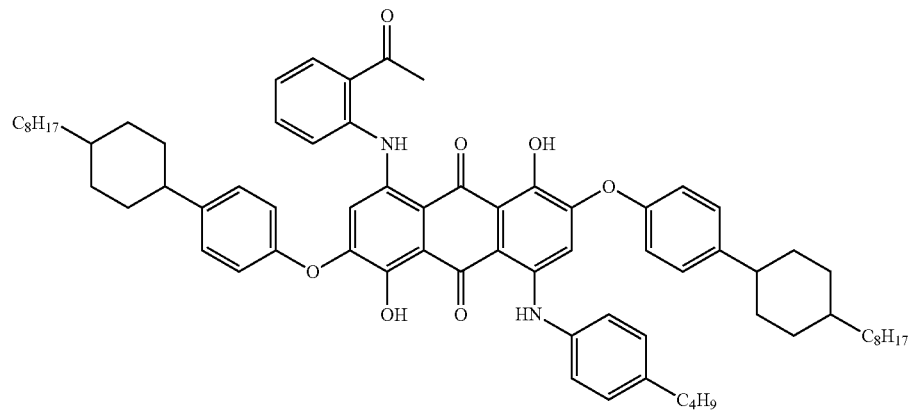
No.35
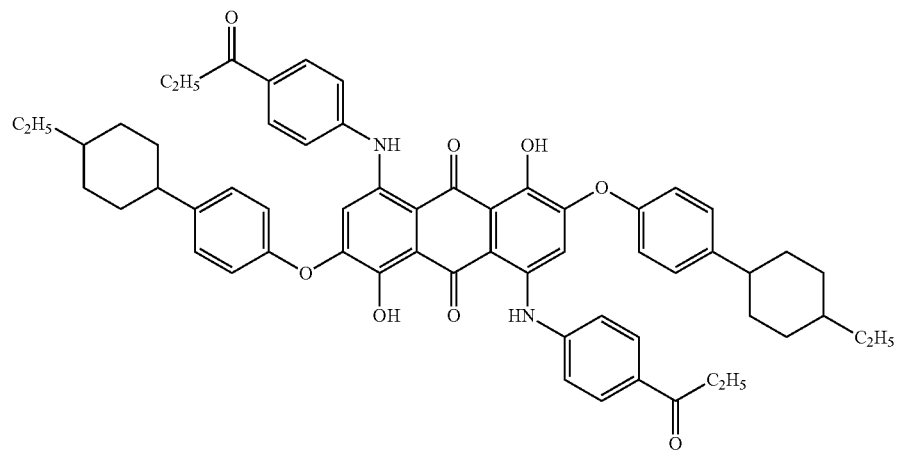
No.36
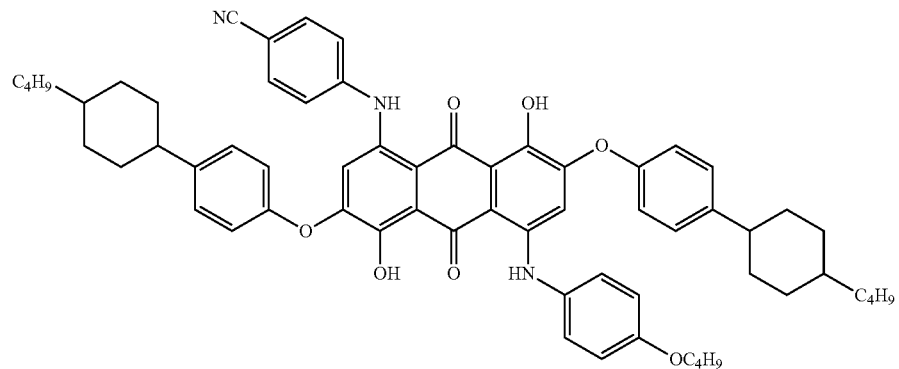
No.37
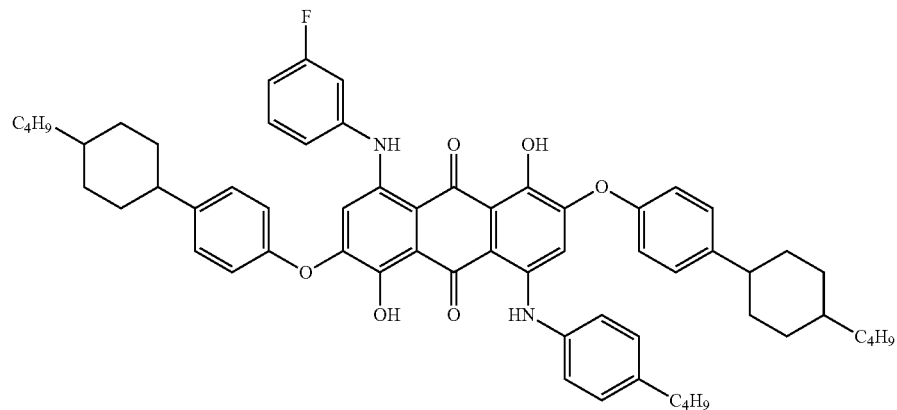

-continued
No.38
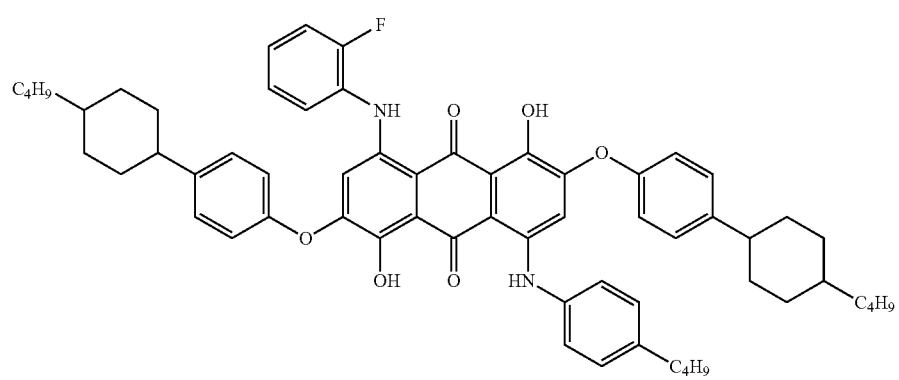
No.39
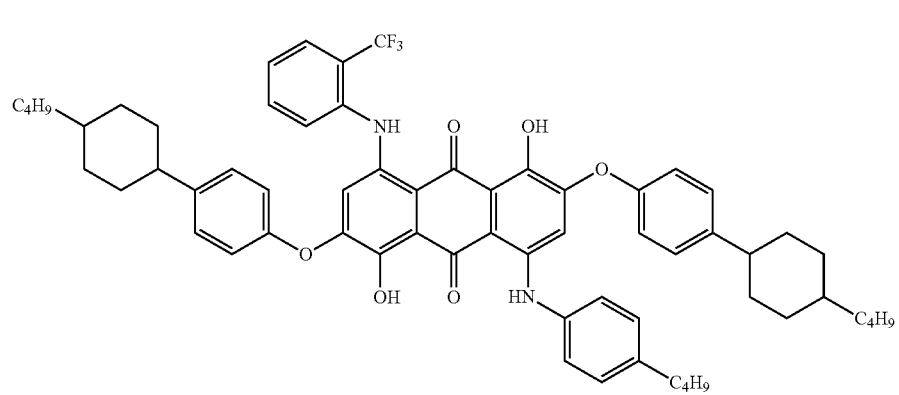
No.40
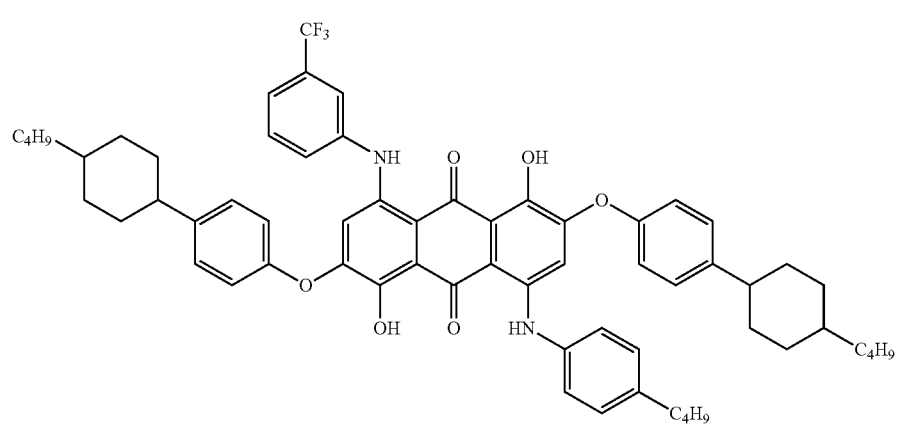
No.41
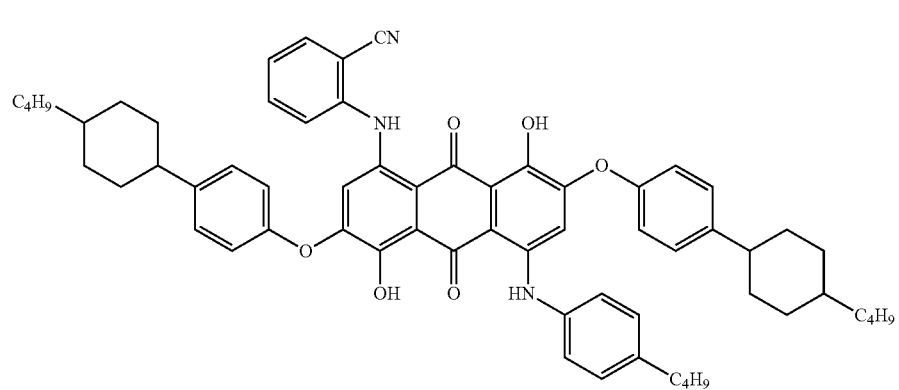

-continued
No.42
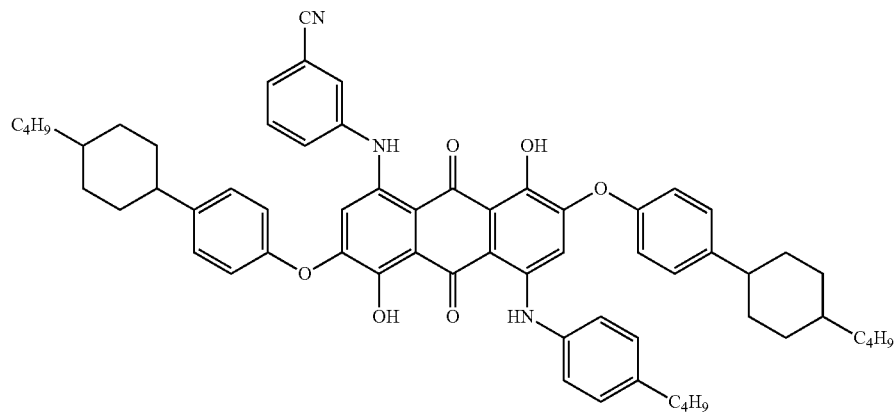
No.43
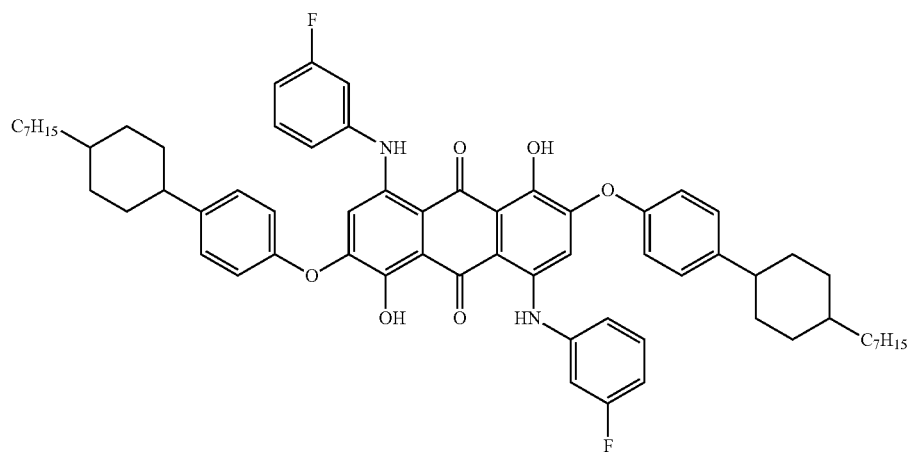
No.44
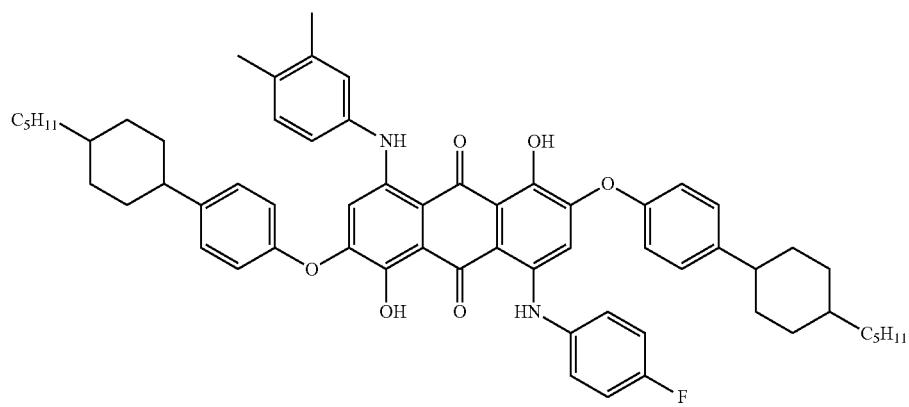
No.45
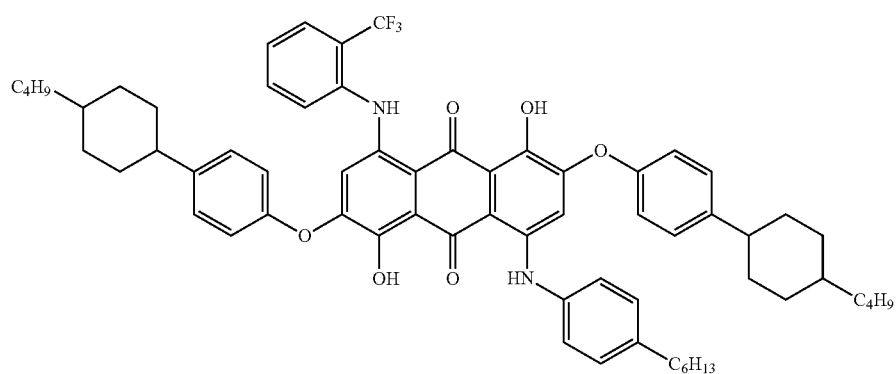

No.46
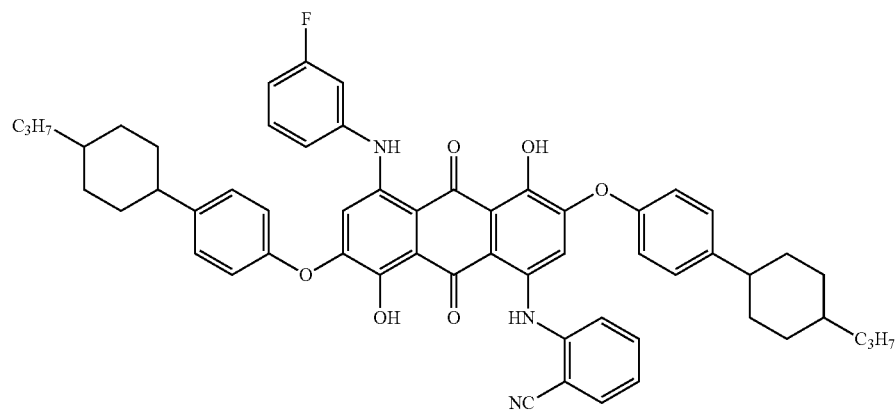
No.47
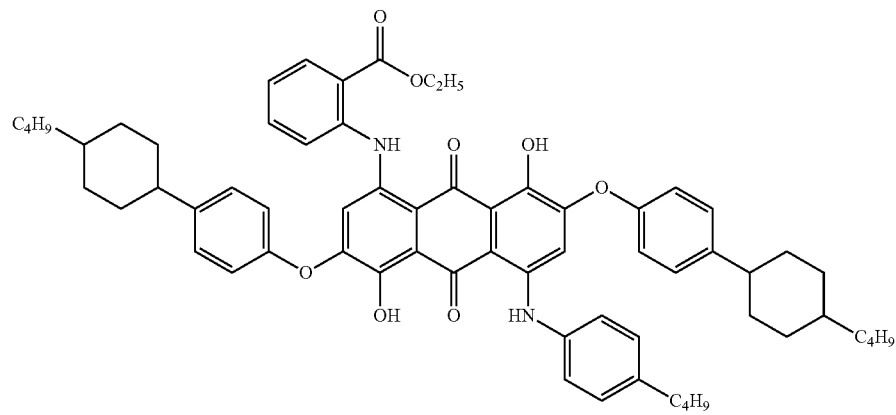
No.48
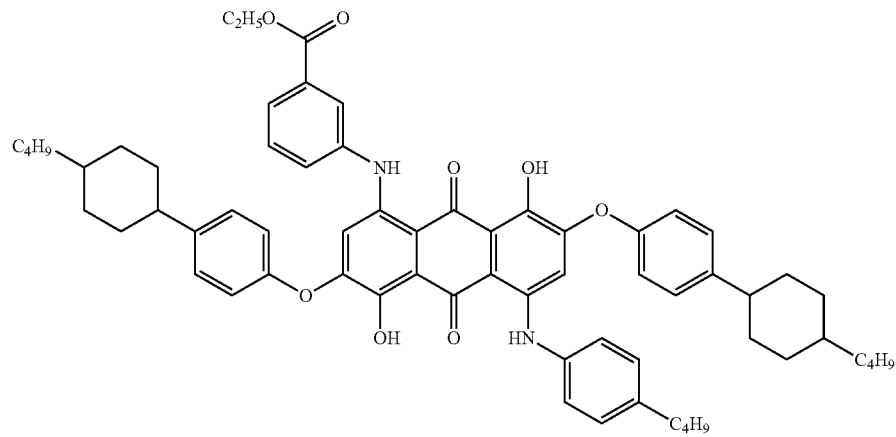
No.49
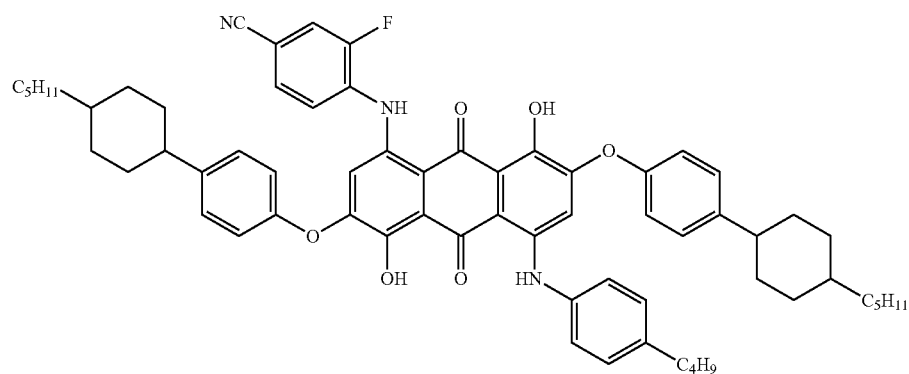

-continued
No.50
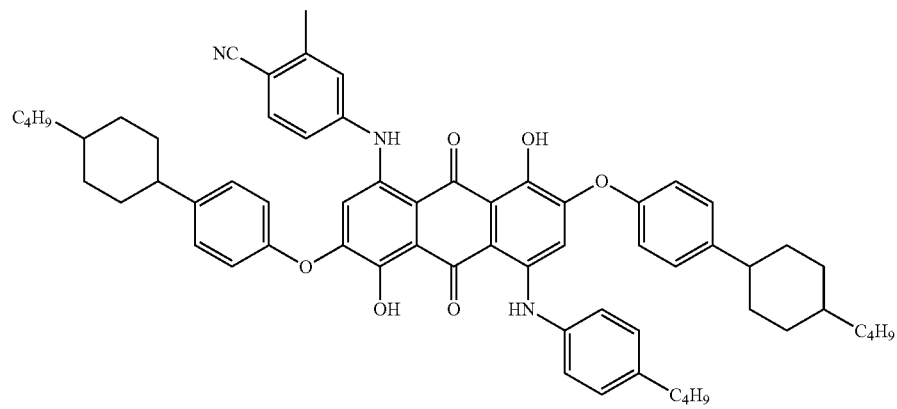
No.51
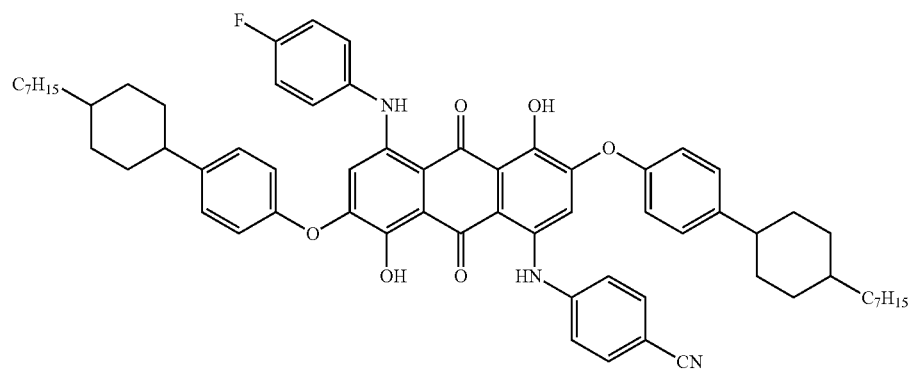
No.52
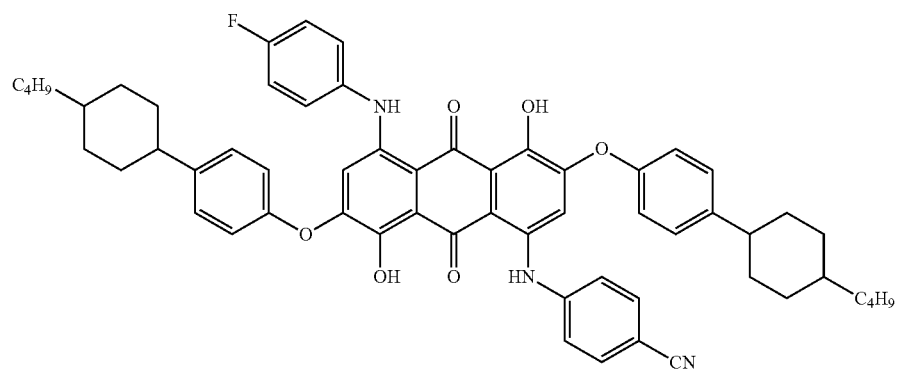
No.53
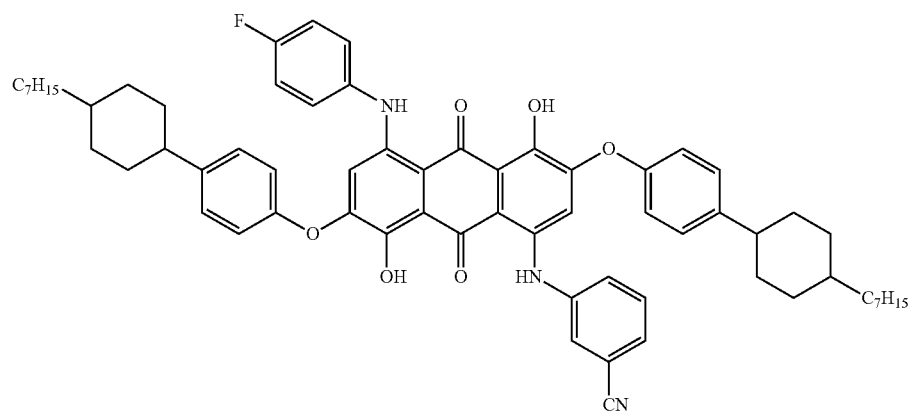

-continued
No.54
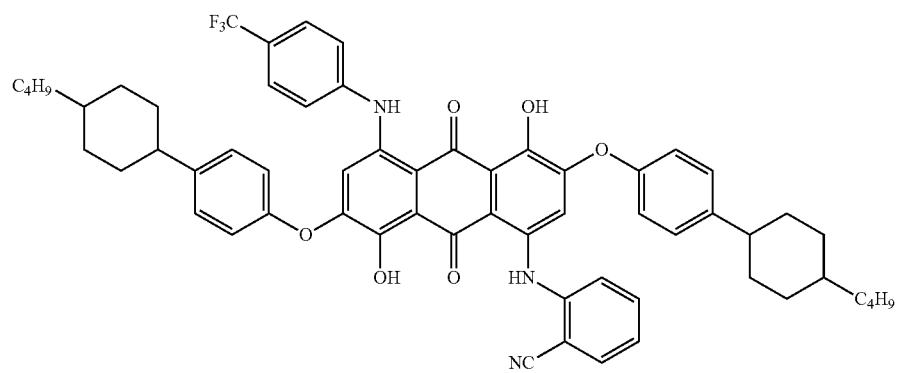
No.55
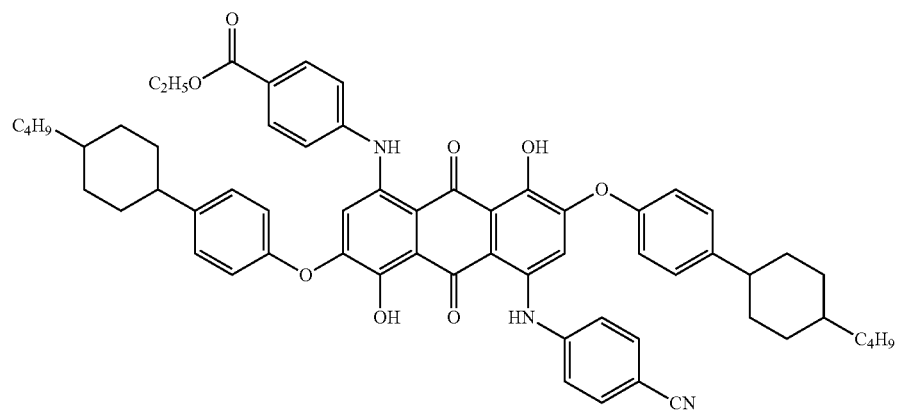
No.56
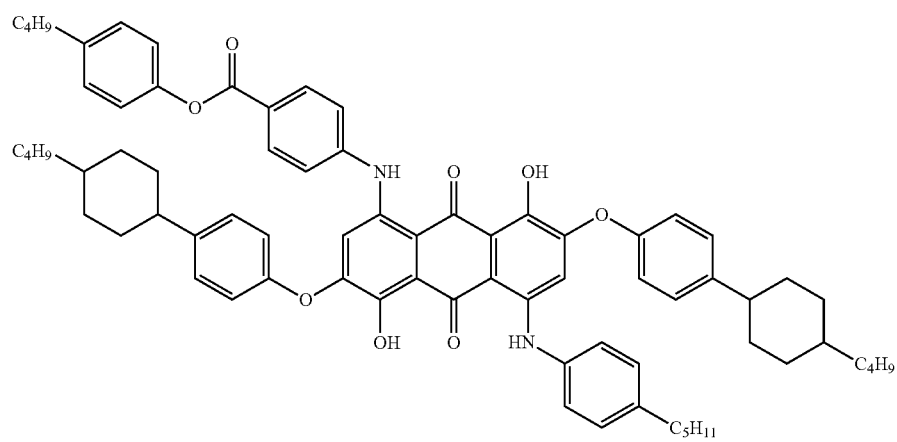
No.57
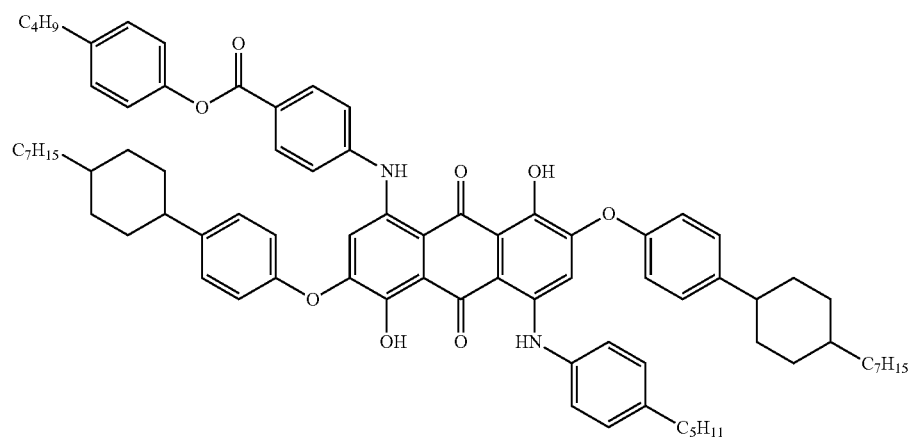

No.58
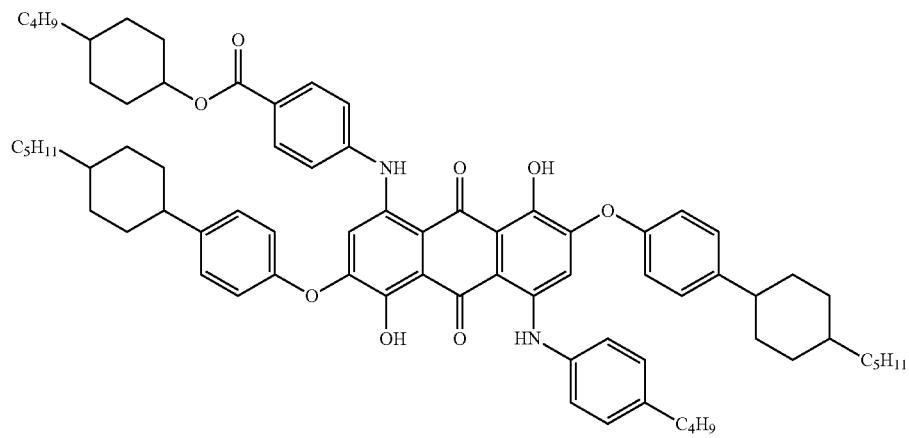
No.59
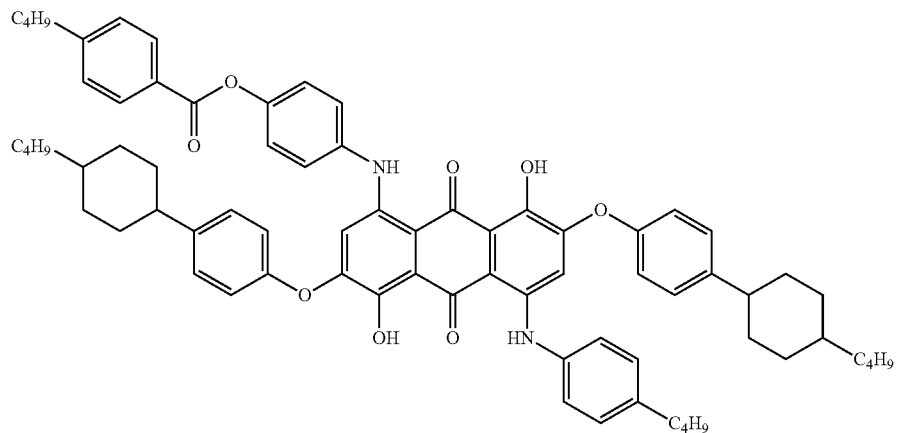
No.60
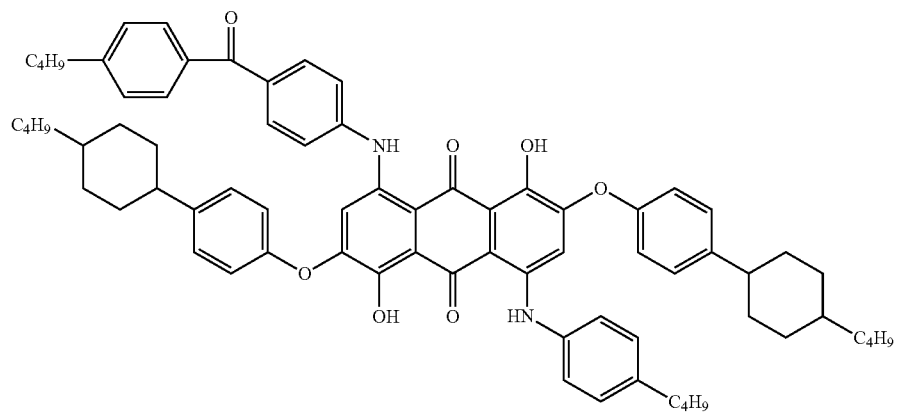

No.61
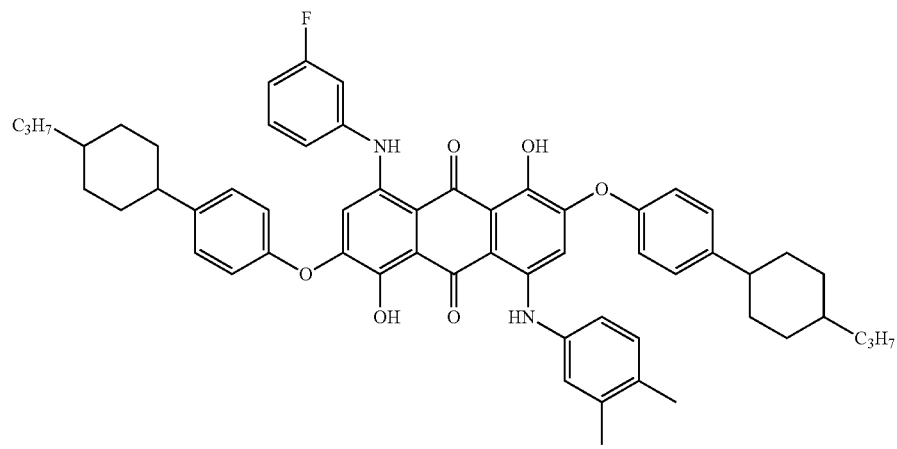
No.62
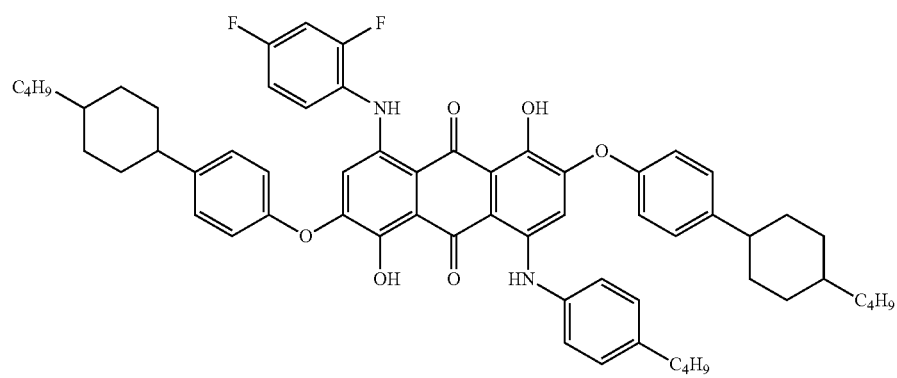
No.63
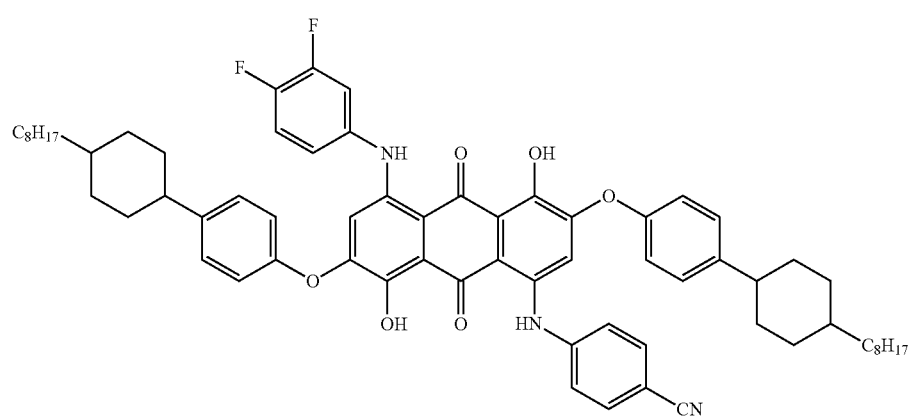

-continued
No.64
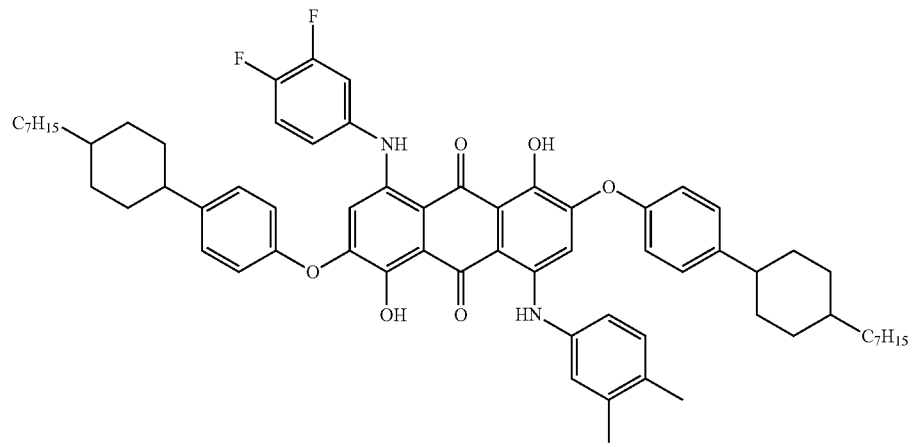
No.65
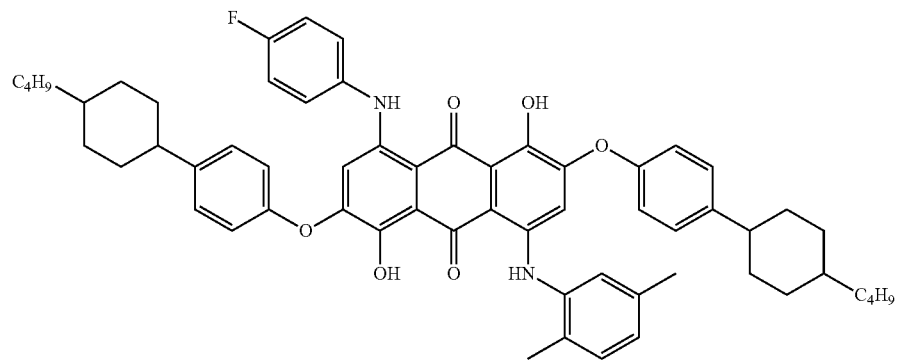
No.66
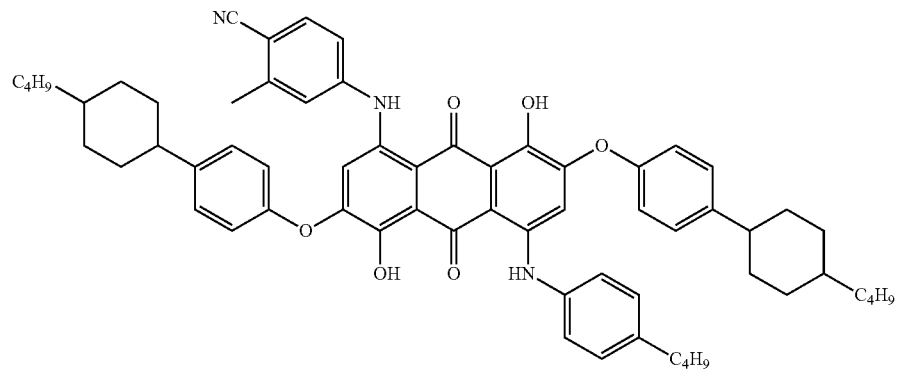
No.67
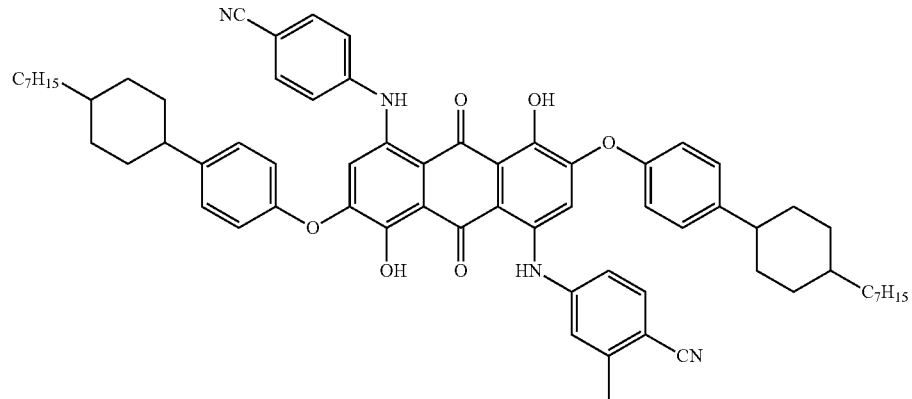

-continued
No.68
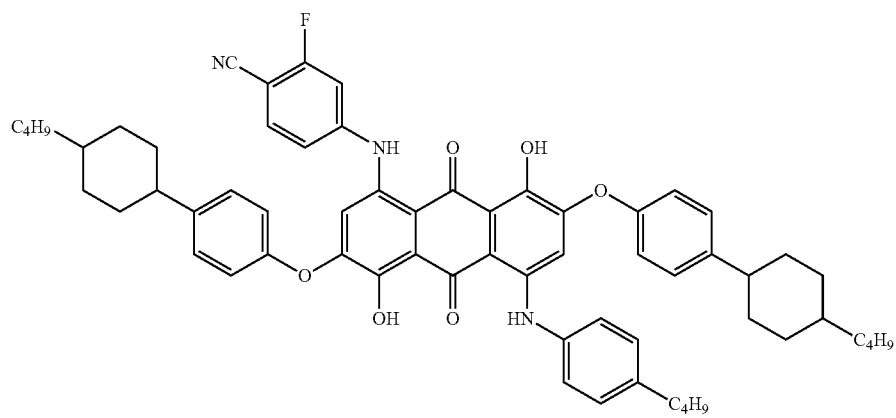
No.69
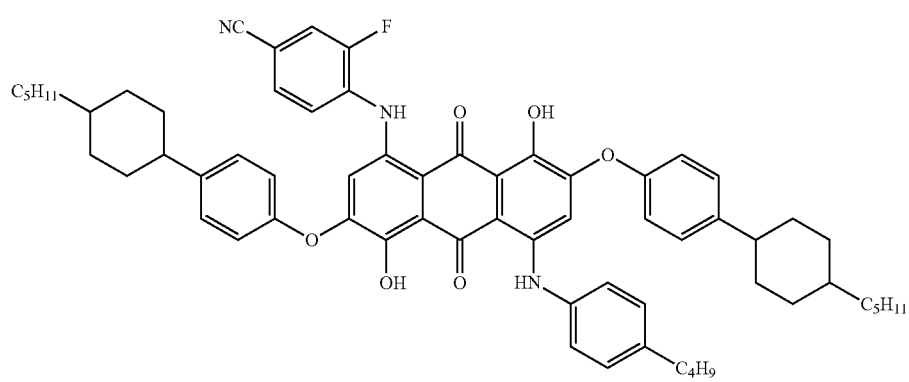
No.70
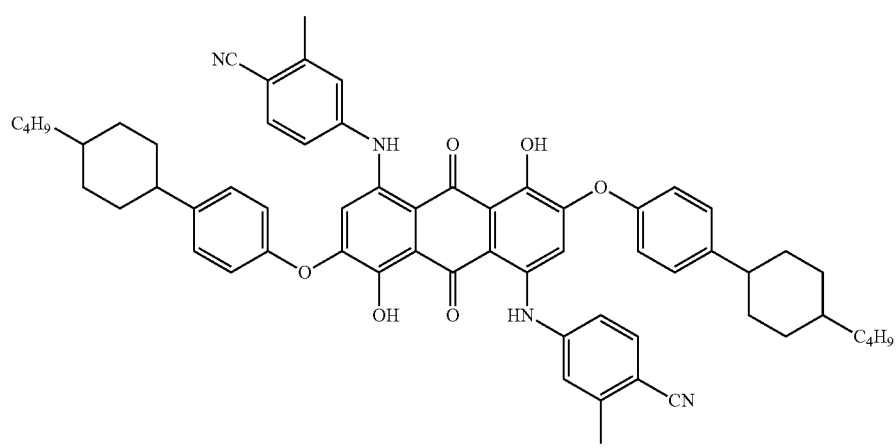
No.71
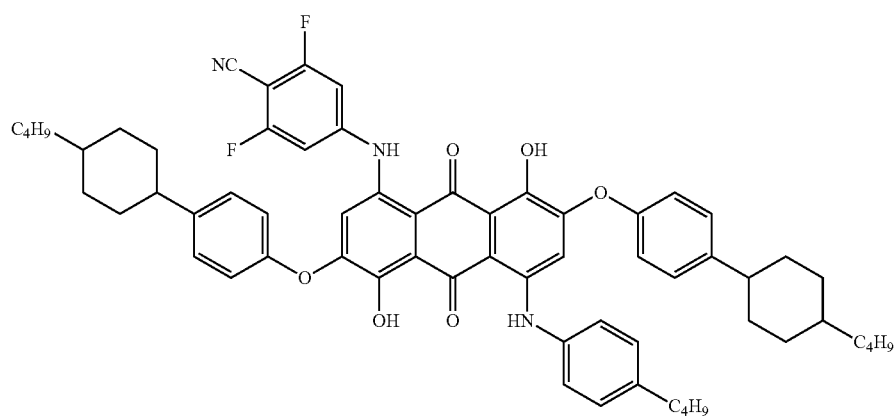

-continued
No.72
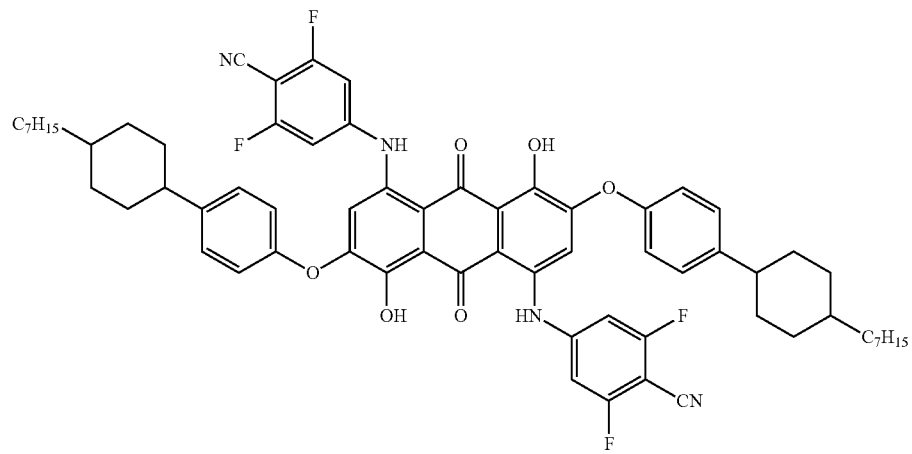
No.73
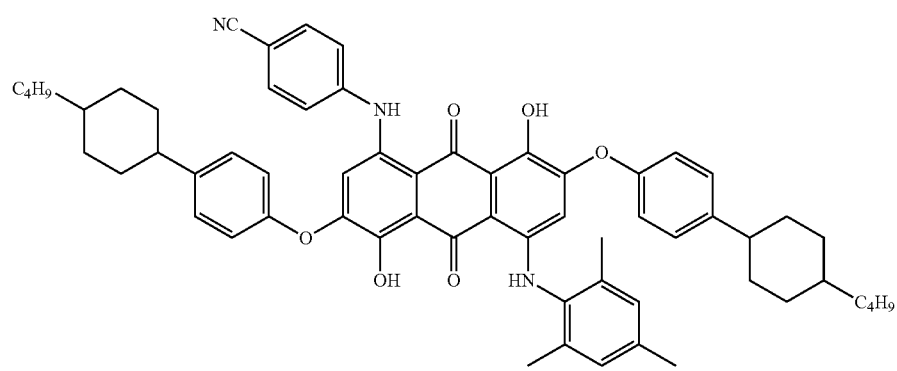
No.74
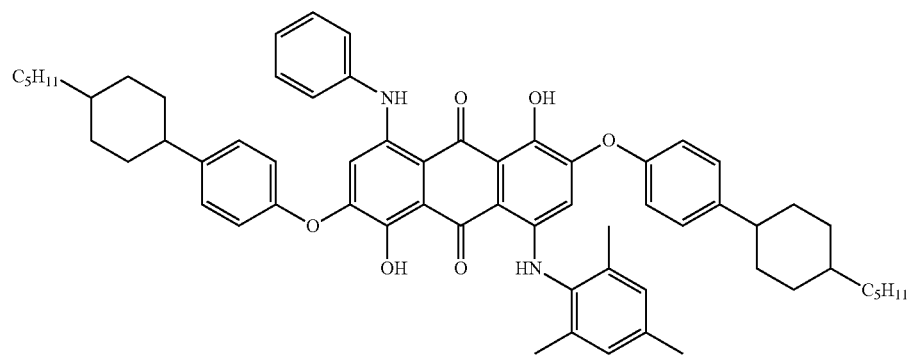
No.75
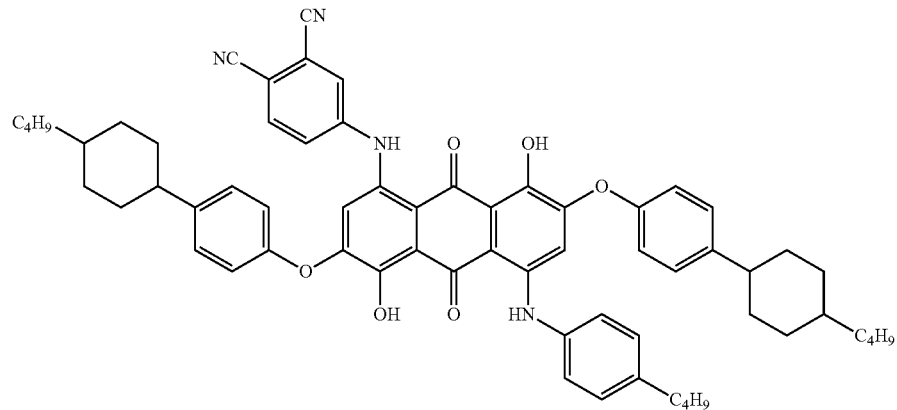

The anthraquinone compound represented by formula (1) preferably has a maximum absorption wavelength region of 650 nm or more.

Next, a method for synthesizing the anthraquinone compound represented by formula (1) of the present invention will be described.

The anthraquinone compound represented by formula (1) can be synthesized, for example, by reacting an anthraquinone compound represented by the following formula (A) synthesized by a conventionally known method described in JPS62-5941A or the like with an iodobenzene derivative represented by the following formula (B) (or alternatively a bromobenzene derivative) at 140 to 160° C. in a solvent such as N-methyl-2-pyrrolidone in the presence of a copper catalyst such as a copper powder under basic conditions such as potassium carbonate.

It is noted that $R_1$ to $R_8$ in the following formulas (A) and (B) have the same meaning as $R_1$ to $R_8$ in formula (1). As another method of this synthesis method, instead of the reaction of introducing, as an iodobenzene derivative, a benzene ring having $R_4$ to $R_6$ as substituents (for example, the reaction exemplified in Examples 1 to 3 described below), a reaction of introducing, as an iodobenzene derivative, a benzene ring having $R_1$ to $R_3$ as substituents (for example, the reaction exemplified in Example 4 described below) may be performed.

A liquid crystal composition of the present invention (hereinafter, also sometimes simply referred to as "composition of the present invention") contains the anthraquinone compound represented by formula (1) and a liquid crystal material.

The content ratio of the anthraquinone compound represented by formula (1) in the liquid crystal composition is not particularly limited, but is preferably 0.5 to 10 parts by mass and more preferably 0.5 to 5 parts by mass with respect to 100 parts by mass of the liquid crystal material. When a dichroic dye (described below) other than the compound represented by formula (1) is used in combination, the total content of the anthraquinone compound represented by formula (1) and the dichroic dye other than the compound represented by formula (1) is preferably in the above range (0.5 to 10 parts by mass) with respect to 100 parts by mass of the liquid crystal material.

The liquid crystal material contained in the liquid crystal composition of the present invention is not particularly limited as long as it is a material having liquid crystallinity (i.e., a compound having liquid crystallinity) such as nematic liquid crystal, cholesteric liquid crystal, or smectic liquid crystal, but among them, nematic liquid crystal is preferable. Examples of the compound having liquid crystallinity include liquid crystal compounds described in pages 154 to 192 and pages 715 to 722 of "*Liquid Crystal Device Handbook*" (edited by the 142nd Committee of the Japan Society for the Promotion of Science, THE NIKKAN KOGYO SHIMBUN, LTD., 1989).

The liquid crystal composition of the present invention may contain a dichroic dye other than the anthraquinone compound represented by formula (1), or an optically active substance that shows or does not show a liquid crystal phase such as a cholesteryl nonanoate, additives such as an ultraviolet absorber and an antioxidant, a photocurable compound, a photopolymerization initiator, and the like.

The photocurable compound that can be contained in the liquid crystal composition of the present invention is not particularly limited as long as it is a compound having a functional group capable of being polymerized by the action of a photopolymerization initiator described below when irradiated with light. Examples of the photocurable compound include a compound having a (meth)acrylate group, a compound having a vinyl group, and a compound having an allyl group. A compound having a (meth)acrylate group is preferable. It is noted that the term "(meth)acrylate" referred to herein means "methacrylate and/or acrylate".

Examples of the (meth)acrylate compound contained in the liquid crystal composition of the present invention include, but are not limited to, a mono(meth)acrylate compound having one (meth)acrylate group in one molecule and a di(meth)acrylate compound having two (meth)acrylate groups in one molecule.

The mono(meth)acrylate compound is preferably a mono (meth)acrylate having a C5-C13 linear, cyclic, or branched alkyl group. Specific examples thereof include linear alkyl mono(meth)acrylates such as pentyl (meth)acrylate, hexyl (meth)acrylate, heptyl (meth)acrylate, octyl (meth)acrylate, nonyl (meth)acrylate, decyl (meth)acrylate, undecyl (meth) acrylate, dodecyl (meth)acrylate, and tridecyl (meth)acrylate; cyclic alkyl mono(meth)acrylates such as isobornyl (meth)acrylate; and branched alkyl mono(meth)acrylates such as 2-methylhexyl (meth)acrylate, 2-ethylhexyl (meth)

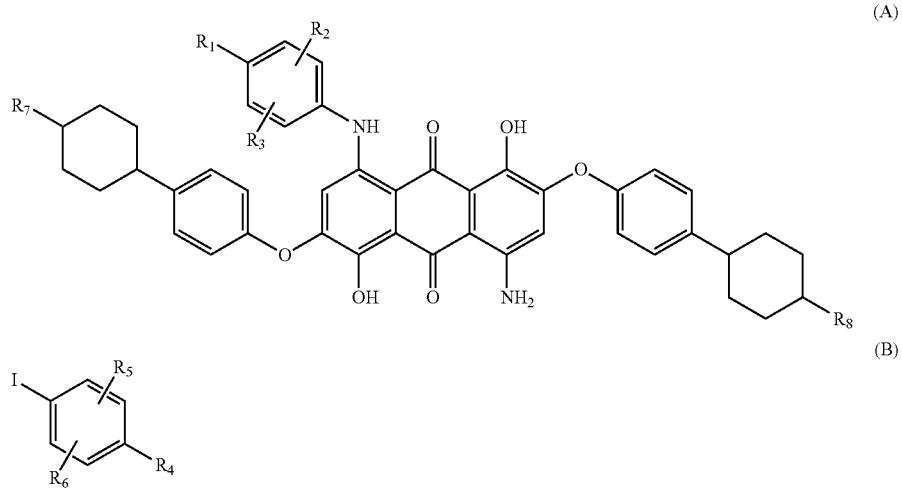

(A)

(B)

acylate, 2-propylhexyl (meth)acylate, 2-methylheptyl (meth)acrylate, 2-ethylheptyl (meth)acrylate, and 2-propylheptyl (meth)acrylate.

Examples of the di(meth)acrylate compound include 1,4-butanediol di(meth)acrylate, 1,5-pentanediol di(meth)acrylate, 1,6-hexanediol di(meth)acrylate, 1,7-heptanediol di(meth)acylate, 1,8-octanediol di(meth)acylate, 1,9-nonanediol di(meth)acrylate, 1,10-decanediol di(meth)acrylate, 1,11-undecanediol di(meth)acrylate, 1,12-dodecanediol di(meth)acrylate, and 1,13-tridecanediol di(meth)acrylate, and further include trialkylene glycol di(meth)acrylates such as triethylene glycol di(meth)acrylate.

In the liquid crystal composition of the present invention, the mono(meth)acrylate compound and the di(meth)acrylate compound may be used in combination. For the ratio in the case of using the mono(meth)acrylate compound and the di(meth)acrylate compound in combination, the mass ratio of the mono(meth)acrylate compound to the di(meth)acrylate compound is preferably 10:90 to 96:4 and more preferably 50:50 to 95:5.

The photopolymerization initiator that can be contained in the composition of the present invention is not particularly limited as long as it is a compound capable of polymerizing a photocurable compound by light irradiation. The photopolymerization initiator is preferably one that does not remain in the cured product after light irradiation and does not cause deterioration of the dichroic dye such as the anthraquinone compound represented by formula (1) in the cured product.

As the photopolymerization initiator, for example, alkylphenone-based photopolymerization initiators such as DAROCURE 1173, IRGACURE 651, and IRGACURE 184, and phosphine oxide-based photopolymerization initiators such as IRGACURE TPO are preferably used.

In the composition of the present invention when containing the photocurable compound and the photopolymerization initiator, the blending ratio of the total of the anthraquinone compound represented by formula (1) and the liquid crystal material to the photocurable compound is preferably 90:10 to 50:50, more preferably 80:20 to 50:50, and still more preferably 60:40 to 50:50 in mass ratio. When the blending ratio of the photocurable compound is set in the above range, it is possible to prevent separation of the liquid crystal material and the photocurable compound before curing by light irradiation and reduction of the light shielding property of the cured product.

In the case of using a dichroic dye (described below) other than the compound represented by formula (1) in combination, the blending ratio of the total of the entire dichroic dye containing the anthraquinone compound represented by formula (1) and the liquid crystal material to the photocurable compound in the composition of the present invention is preferably in the above range (90:10 to 50:50 in mass ratio), and the more preferred range and the still more preferred range are also the same as those described above.

The content of the photopolymerization initiator in the composition of the present invention when containing the photocurable compound and the photopolymerization initiator is preferably 0.1 to 5 parts by mass with respect to 100 parts by mass of the photocurable compound.

A dichroic dye other than the anthraquinone compound represented by formula (1) can be used in combination in the composition of the present invention.

The dichroic dye that can be used in combination is not particularly limited, and may be selected from, for example, an azo dye, an anthraquinone dye, a perylene dye, a quinophthalone dye, a merocyanine dye, an azomethine dye, a phthaloperylene dye, an indigo dye, an azulene dye, a dioxazine dye, a polythiophene dye, and the like. Specific examples thereof include those described in "Dichroic dyes for Liquid Crystal Display" (A. V. Ivashchenko, C R C, 1994). Among them, an azo dye, an anthraquinone dye, a perylene dye, or a quinophthalone dye is preferably used in combination, and an azo dye or an anthraquinone dye is more preferably used in combination.

In the case of using a dichroic dye other than the anthraquinone compound represented by formula (1) in combination, the content of the anthraquinone compound represented by formula (1) in the entire dichroic dye is not particularly limited as long as the effect of the present invention is not impaired. The amount thereof is preferably 1 to 80 mass %, more preferably 5 to 70 mass %, and still more preferably 10 to 50 mass %.

In the composition of the present invention, light stabilizers such as benzotriazole-based, benzophenone-based, and hindered amine-based light stabilizers, antioxidants such as phosphite-based and hindered phenol-based antioxidants, a thermal polymerization inhibitor, a thiol compound, a photosensitizing agent, a photosensitizer, a chain transfer inhibitor, a polymerization inhibitor, an adhesiveness imparting agent, an antifoaming agent, a crosslinking agent, a surfactant, a thermosetting accelerator, a thermoplastic resin, a thermosetting resin, a thickener such as a urethane diacrylate, and the like may be further used in combination.

In order to control a cell gap as the light control element, a spherical or cylindrical spacer, such as silica, glass, plastics, or ceramics, may be added. The cell gap in this case can be set in a range of 2 to 100 μm.

The liquid crystal composition for light control of the present invention can be obtained by mixing and stirring the anthraquinone compound represented by formula (1) and the liquid crystal material, which are essential components, and other optional components, such as the photocurable compound and the photopolymerization initiator, which are added as necessary. The mixing and stirring may be performed, in the simplest way, by placing all the constituent components in a container and manually stirring them, but it is effective to stir them using equipment such as a magnetic stirrer.

When the composition of the present invention containing the photocurable compound and the photopolymerization initiator is irradiated with light, a cured product of the liquid crystal composition, in which the photocurable compound component is cured (polymerized), can be obtained. It is noted that the "cured product" in the present invention means a state where the functional group of the photocurable compound is polymerized or copolymerized by light irradiation, and does not necessarily mean a cured product in which the anthraquinone compound represented by formula (1), the liquid crystal material, or the like has contributed to the curing reaction.

A light source for the light irradiation is not particularly limited as long as it is a light source capable of emitting light having a wavelength to be absorbed by the photopolymerization initiator. Preferable examples of the light source include high-pressure mercury lamp, a metal halide lamp, a xenon lamp, and a halogen lamp that are capable of emitting ultraviolet rays.

In the light control element of the present invention, a layer of the liquid crystal composition or a photocured product thereof is sandwiched between a pair of substrates disposed opposite to each other, at least one of which is a transparent substrate having a transparent electrode. Here, examples of the substrate include a colorless transparent, colored transparent, or opaque substrate such as an inorganic transparent material such as glass or quartz, a metal, a metal oxide, a semiconductor, ceramics, a plastic plate, or a plastic film. The electrode is formed on the substrate by, for example, forming a thin film of a metal oxide, a metal, a semiconductor, an organic conductive material, or the like on the entire surface or a part of the substrate by a coating method, a printing method, a vapor deposition method such as sputtering, or the like that has been known. In particular, in order to obtain a light control element having a large area, it is desirable to use an electrode substrate in which an ITO (indium oxide, tin oxide) electrode is formed on a transparent polymer film such as PET using a vapor deposition method such as sputtering, a printing method, or the like from the viewpoint of productivity and processability. It is a more preferable embodiment that both of the pair of substrates are transparent substrates having a transparent electrode. Wiring may be provided on the substrate for connecting between the electrodes or between the electrodes and the outside. For example, a segment driving electrode substrate, a matrix driving electrode substrate, an active matrix driving electrode substrate, or the like may be used. The surface of the electrode provided on the substrate may be entirely or partially covered with a protective film or an alignment film made of an organic compound such as a polyimide, a polyamide, a silicone, or a cyan compound, an inorganic compound such as $SiO_2$, $TiO_2$, or $ZrO_2$, or a mixture thereof.

By using the plastic film as a substrate, a flexible and lightweight light control element can be obtained. Therefore, it is possible to use the light control element by sandwiching the light control element between a pair of planar or curved substrates of glass, hard plastic, or the like with an adhesive layer such as polyvinyl butyral, vinyl acetate, a double-sided tape, or an adhesive. Alternatively, the light control element can be used by being attached to the surface of one planar or curved substrate of glass, hard plastic, or the like with a double-sided tape, an adhesive, or the like. Alternatively, the light control element may be sandwiched between soft plastic substrates or be attached to one side or both sides. A protective layer such as a hard coat, an ultraviolet rays cut layer, an infrared rays cut layer, or a half mirror may be provided on the substrate surface opposite to the electrode surface of the light control element, or a color filter may be laminated on the light control element or a polarizer filter may be attached to the light control element. Alternatively, the light control element may be laminated with an electroluminescence display element, a light emitting diode display element, an electrochromic display element, or another liquid crystal display element.

A drive device for applying a voltage to the light control element of the present invention may be a device which is capable of applying a DC voltage of 2 to 100 V or an AC voltage of 10 to 1000 Hz and which opens or short-circuits between electrodes when no voltage is applied. This drive device may include a voltage application circuit for segment driving, a voltage application circuit for matrix driving, a voltage application circuit for active matrix, and the like.

Since the anthraquinone compound represented by formula (1) of the present invention has a maximum absorption wavelength region in a long wavelength region of 650 nm or more and is excellent in spectral characteristics, by using this compound, it is possible to obtain a light control element in which light leakage at the time of light shielding is suppressed and which is excellent in contrast. Therefore, the light control element of the present invention is optimal for building materials such as windows, partitions, and doors, in-vehicle materials such as windows and sunroofs, materials for exhibits such as displays and show windows displaying characters, numbers, and the like, for example.

EXAMPLES

Hereinafter, the present invention will be described in more detail with reference to Examples; however, the present invention is not limited thereto. It is noted that the terms "part(s)" and "%" in the present text are on a mass basis unless otherwise specified. The maximum absorption wavelength in Examples is a value measured with a spectrophotometer "UV-3150" manufactured by SHIMADZU CORPORATION.

Example 1 (Synthesis of Compound Represented by No. 3 in Specific Compound Examples)

To 0.9 parts of a compound represented by the following formula (C) synthesized by the method described in JPS62-5941A (Patent Literature 5), 20 parts of NMP, 0.02 parts of copper powder, 0.02 parts of copper iodide, 2.0 parts of iodobenzene, 0.02 pails of potassium carbonate, and 0.15 parts of sodium acetate were added, the mixture was stirred at 140 to 150° C. for 12 hours, the reaction solution was then cooled to 25° C., 200 parts of methanol was added, and the mixture was stirred for 1 hour. The reaction product was collected by filtration, washed with methanol, and then dried in a hot air dryer at 50° C. for 24 hours. The obtained crude product was dissolved in toluene, and column purification was performed using toluene as a developing solvent. The solvent was distilled off under reduced pressure from the solution after purification, and the resultant was dried in a hot air dryer at 50° C. for 24 hours to obtain 0.3 parts of the compound represented by No. 3 in the above specific compound examples as a blue solid.

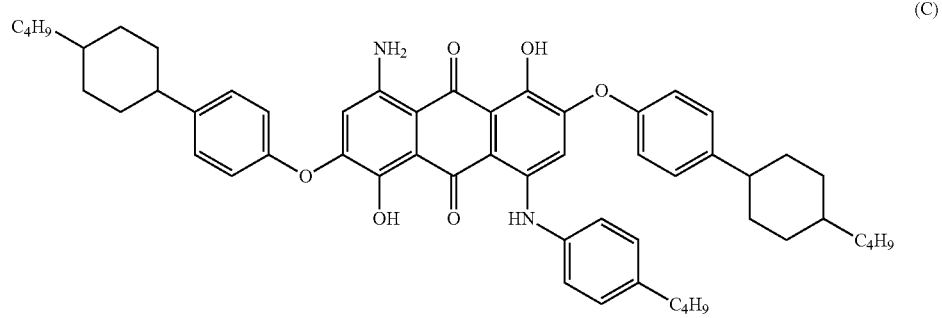

(C)

Example 2 (Synthesis of Compound Represented by No. 14 in Specific Compound Examples)

The same procedure as in Example 1 was performed to obtain 0.4 parts of the compound represented by No. 14 in specific compound examples as a blue solid, except that 2.1 parts of 2-methyliodobenzene was used instead of 2.0 parts of iodobenzene.

Example 3 Synthesis of Compound Represented by No. 9 in Specific Compound Examples)

The same procedure as in Example 1 was performed to obtain 0.5 parts of the compound represented by No. 9 in specific compound examples as a blue solid, except that 3.2 parts of 1-((2-ethylhexyl)oxy)-4-iodobenzene was used instead of 2.0 parts of iodobenzene.

Example 4 (Synthesis of Compound Represented by No. 25 in Specific Compound Examples)

The same procedure as in Example 1 was performed to obtain 0.3 parts of the compound represented by No. 25 in specific compound examples as a blue solid, except that 2.2 parts of 4-iodobenzonitrile was used instead of 2.0 parts of iodobenzene.

Example 5 (Synthesis of Compound Represented by No. 19 in Specific Compound Examples)

The same procedure as in Example 1 was performed to obtain 0.2 parts of the compound represented by No. 19 in specific compound examples as a blue solid, except that 2.4 parts of 4-iodochlorobenzene was used instead of 2.0 parts of iodobenzene.

Example 6 (Synthesis of Compound Represented by No. 26 in Specific Compound Examples)

The same procedure as in Example 1 was performed to obtain 0.4 parts of the compound represented by No, 26 in specific compound examples as a blue solid, except that 2.8 parts of ethyl 4-iodobenzoate was used instead of 2.0 parts of iodobenzene.

Example 7 (Synthesis of Compound Presented by No. 41 in Specific Compound Examples)

The same procedure as in Example 1 was performed to obtain 0.2 parts of the compound represented by No. 41 in specific compound examples as a blue solid, except that 2.3 parts of 2-iodobenzonitrile was used instead of 2.0 parts of iodobenzene.

Example 8 Synthesis of Compound Represented by No. 49 in Specific Compound Examples)

The same procedure as in Example 1 was performed to obtain 0.4 parts of the compound represented by No. 49 in specific compound examples as a blue solid, except that 0.9 parts of a compound represented by the following formula (E) was used instead of 0.9 parts of the compound represented by the above formula (C) and 2.0 parts of 4-bromo-3-fluorobenzonitrile was used instead of 2.0 parts of iodobenzene.

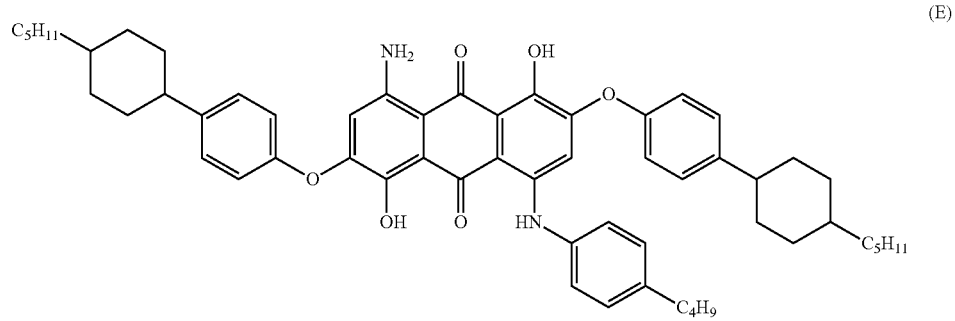

(E)

Example 9 Synthesis of Compound Represented by No. 33 in Specific Compound Examples)

The same procedure as in Example 1 was performed to obtain 0.3 parts of the compound represented by No. 33 in specific compound examples as a blue solid, except that 2.5 parts of 3-iodoacetophenone was used instead of 2.0 parts of iodobenzene.

Example 10 (Synthesis of Compound Represented by No. 20 in Specific Compound Examples)

The same procedure as in Example 1 was performed to obtain 0.3 parts of the compound represented by No. 20 in specific compound examples as a blue solid, except that 0.9 parts of a compound represented by the following formula (F) was used instead of 0.9 parts of the compound represented by the above formula (C) and 2.2 parts of 4-iodofluorobenzene was used instead of 2.0 parts of iodobenzene.

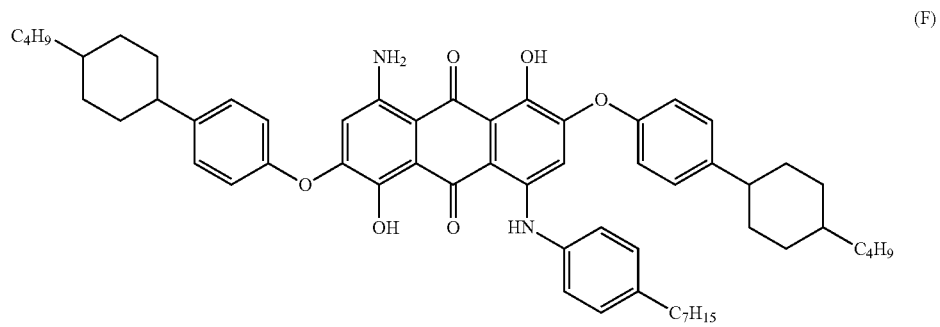

(F)

Example 11 (Synthesis of Compound Represented by No. 28 in Specific Compound Examples)

The same procedure as in Example 1 was performed to obtain 0.3 parts of the compound represented by No. 28 in specific compound examples as a blue solid, except that 0.9 parts of a compound represented by the following formula (G) was used instead of 0.9 parts of the compound represented by the above formula (C) and 2.3 parts of 4-bromobenzotrifluoride was used instead of 2.0 parts of iodobenzene.

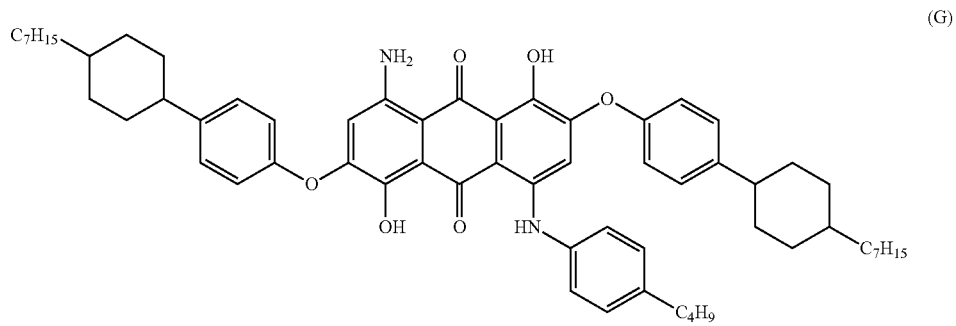

(G)

Example 12 (Synthesis of Compound Represented by No. 67 in Specific Compound Examples)

The same procedure as in Example 1 was performed to obtain 0.3 parts of the compound represented by No. 67 in specific compound examples as a blue solid, except that 0.9 parts of a compound represented by the following formula (H) was used instead of 0.9 parts of the compound represented by the above formula (C) and 2.3 parts of 4-iodobenzonitrile was used instead of 2.0 parts of iodobenzene.

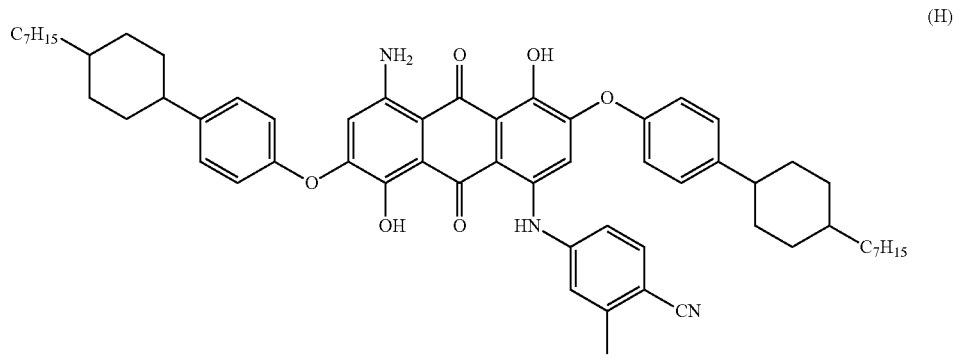

(H)

Comparative Example 1 (Synthesis of Comparative Example Compound)

The compound represented by the above formula (C) was obtained by the method described in JPS62-5941A (Patent Literature 5).

(Evaluation of λMax of Anthraquinone Compound)

Each of the anthraquinone compounds obtained in Examples 1 to 12 and Comparative Example 1 was weighed in an amount of 10 mg and dissolved in 20 mL of N-methylpyrrolidone. The solution was collected in an amount of 1 mL and diluted with 50 mL of toluene, and the maximum absorption wavelength (λmax) was measured with a spectrophotometer "UV-3150" manufactured b SHIMADZU CORPORATION. The results are shown in Table 1 and Table 2.

TABLE 1

Maximum absorption wavelength (λmax) of anthraquinone compound

| | Compound No | Structure | λ max |
|---|---|---|---|
| Example 1 | 3 | 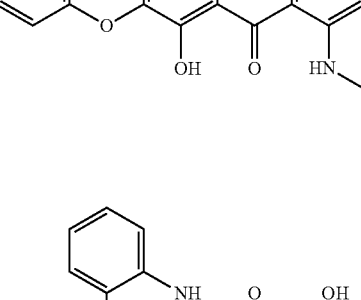 | 656 nm |
| Example 2 | 14 | 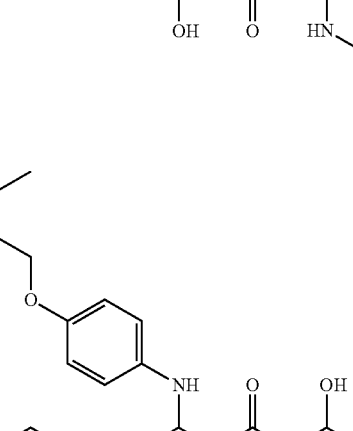 | 654 nm |
| Example 3 | 9 | 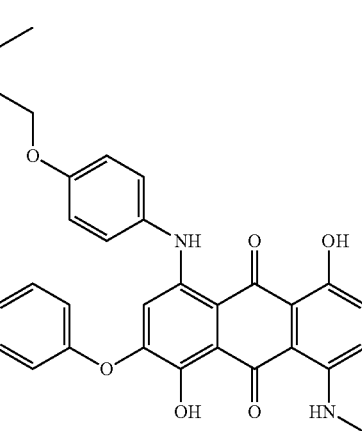 | 658 nm |

TABLE 1-continued

Maximum absorption wavelength (λmax) of anthraquinone compound

| | Compound No | Structure | λ max |
|---|---|---|---|
| Example 4 | 25 | *(anthraquinone structure)* | 652 nm |
| Comp. Example 1 | (C) | *(anthraquinone structure)* | 628 nm |

TABLE 2

Maximum absorption wavelength (λmax) of anthraquinone compound

| | Compound No | Structure | λ max |
|---|---|---|---|
| Example 5 | 19 | *(anthraquinone structure)* | 653 nm |

TABLE 2-continued

Maximum absorption wavelength (λmax) of anthraquinone compound

| Compound No | Structure | λ max |
|---|---|---|
| Example 6  26 | | 654 nm |
| Example 7  41 | | 651 nm |
| Example 8  49 | | 651 nm |

TABLE 2-continued

Maximum absorption wavelength (λmax) of anthraquinone compound

| Compound No | Structure | λ max |
|---|---|---|
| Example 9 | 33 | 653 nm |
| Example 10 | 20 | 653 nm |
| Example 11 | 28 | 650 nm |

TABLE 2-continued

Maximum absorption wavelength (λmax) of anthraquinone compound

| Compound No | | Structure | λ max |
|---|---|---|---|
| Example 12 | 67 | 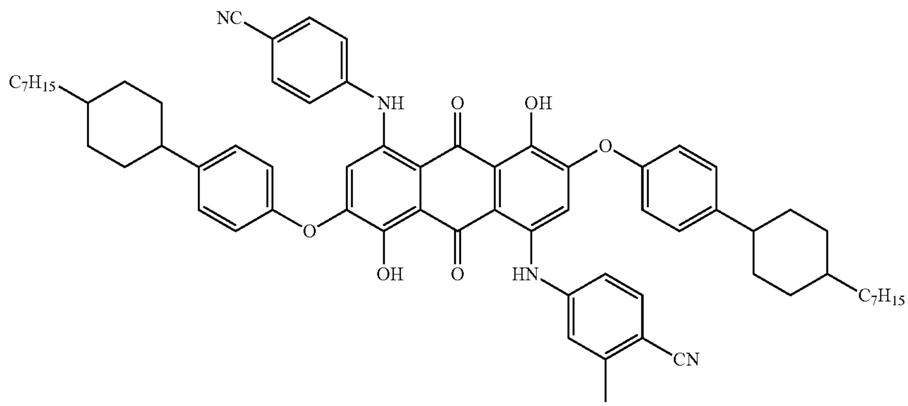 | 650 nm |

From Table 1 and Table 2, it was found that the anthraquinone compound of the present invention had a maximum absorption wavelength (λmax) of 650 nm or more and had a maximum absorption wavelength in a longer wavelength region than the compound of Comparative Example 1.

Example 13 (Preparation of Liquid Crystal Composition of Present Invention)

A liquid crystal composition of the present invention was prepared by mixing 0.006 pails of the compound represented by No. 3 in specific compound examples obtained in Example 1 and liquid crystal materials (0.306 parts of 1-cyano-4'-n-pentylbiphenyl, 0.15 parts of 1-cyano-4'-n-heptylbiphenyl, 0.096 parts of 1-cyano-4'-n-octyloxybiphenyl, and 0.048 parts of 1-cyano-4''-n-pentylterphenyl) at room temperature.

Examples 14 to 24 (Preparation of Liquid Crystal Compositions of Present Invention)

Liquid crystal compositions of the present invention were each prepared in accordance with Example 13, except that the compound represented by No. 3 in specific compound examples obtained in Example 1 was replaced with the compounds represented by No. 14, No. 9, No. 25, No. 19, No. 26, No. 41, No. 49, No. 33, No. 20, No. 28, and No. 67 in specific compound examples obtained in Examples 2 to 12, respectively.

Comparative Example 2 (Preparation of Liquid Crystal Composition for Comparison)

A liquid crystal composition for comparison was prepared in accordance with Example 13, except that the compound represented by No 3 in specific compound examples obtained in Example 1 was changed to a compound of No. 8 represented by the following formula (D) and described in JPH04-2641493A.

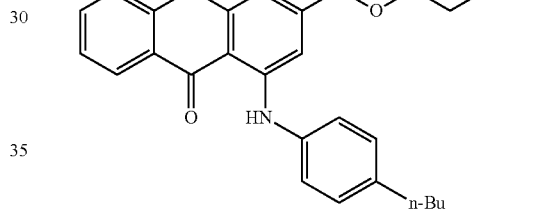
(D)

Examples 25 to 36 and Comparative Example 3 (Production of Light Control Elements of Present Invention and Light Control Element for Comparison)

The liquid crystal compositions obtained in Examples 13 to 24 and Comparative Example 2 were each encapsulated in an element made of two upper and lower glass substrates each having a transparent electrode with an inter-substrate gap of 15 Lim, in which the surface of each glass substrate in contact with a liquid crystal was rubbed with a poly amide-based resin and was subjected to a homogeneous orientation treatment. In the element subjected to the orientation treatment, the liquid crystal was in a homogeneously oriented state when no voltage was applied, and dye molecules were also in the same orientation according to the host liquid crystal.

(Contrast Evaluation of Light Control Elements of Present Invention and Comparative Example)

For the light control elements obtained in Examples 25 to 36 and Comparative Example 3, a transmittance (Kz) of linearly polarized light parallel to the orientation direction and a transmittance (Ky) of polarized light perpendicular to the orientation direction were measured, and a contrast (C) at 650 nm was determined from the following formula. The results are shown in Table 3 and Table 4.

$C=Ky/Kz$

TABLE 3

Maximum absorption wavelength of anthraquinone compound, and contrast of light control element

|  | Compound No | λ max(nm) | C (650 nm) |
|---|---|---|---|
| Example 25 | 3 | 656 nm | 10.5 |
| Example 26 | 14 | 654 nm | 10.3 |
| Example 27 | 9 | 658 nm | 10.1 |
| Example 28 | 25 | 652 nm | 12.1 |
| Comp. Example 3 | Formula (D) | 665 nm | 7.0 |

TABLE 4

Maximum absorption wavelength of anthraquinone compound, and contrast of light control element

|  | Compound No | λ max (nm) | C (650 nm) |
|---|---|---|---|
| Compound No 29 | 19 | 653 nm | 11.2 |
| Compound No 30 | 26 | 654 nm | 12.1 |
| Compound No 31 | 41 | 651 nm | 11.4 |
| Compound No 32 | 49 | 651 nm | 10.8 |
| Compound No 33 | 33 | 653 nm | 10.8 |
| Compound No 34 | 20 | 653 nm | 11.8 |
| Compound No 35 | 28 | 650 nm | 11.7 |
| Compound No 36 | 67 | 650 nm | 10.6 |

As shown in Table 3 and Table 4, it was found that the light control elements of Examples 25 to 36 obtained using the anthraquinone compound of the present invention had substantially the same maximum absorption wavelength as the light control element of Comparative Example, but showed a higher contrast, and both an increase in wavelength and a high contrast could be realized.

Example 37 (Production of Black Light Control Element)

A liquid crystal composition was prepared by mixing 0.003 parts of the compound represented by No. 14 in specific compound examples obtained in Example 2, 0.015 parts of LCD212 (i.e., an anthraquinone-based compound, manufactured by Nippon Kayaku Co., Ltd.), 0.008 parts of a dye compound represented by the following formula (X), 0.306 parts of 1-cyano-4'-n-pentylbiphenyl, 0.15 parts of 1-cyano-4'-n-heptylbiphenyl, 0.096 parts of 1-cyano-4'-n-octyloxybiphenyl, and 0.048 parts of 1-cyano-4''-n-pentylterphenyl at room temperature. The obtained liquid crystal composition was encapsulated in an element made of two upper and lower glass substrates each having a transparent electrode with an inter-substrate gap of 15 µm, in which the surface of each glass substrate in contact with a liquid crystal was rubbed with a poly amide-based resin and was subjected to a homogeneous orientation treatment, thereby producing a black light control element. In the element obtained as described above, the liquid crystal was in a homogeneously oriented state when no voltage was applied, and dye molecules were also in the same orientation according to the liquid crystal.

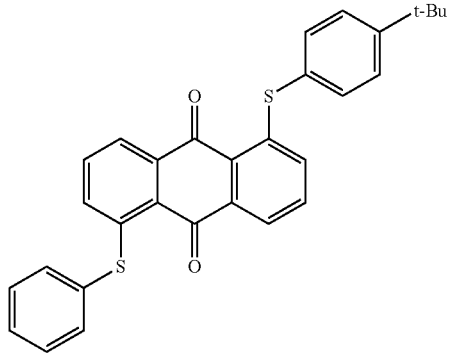

Example 38 (Production of Black Light Control Element)

A liquid crystal composition of the present invention was prepared by stirring 0.467 parts of isobornyl acrylate (manufactured by OSAKA ORGANIC CHEMICAL INDUSTRY LTD.) as a monofunctional monomer of a photocurable compound, 0.024 parts of triethylene glycol dimethacrylate (manufactured by SHIN-NAKAMURA CHEMICAL CO. LTD.) as a bifunctional monomer of a photocurable compound, 0.255 parts of 1-cyano-4'-n-pentylbiphenyl, 0.125 parts of 1-cyano-4'-n-heptylbiphenyl, 0.080 parts of 1-cyano-4'-n-octyloxybiphenyl, and 0.040 parts of 1-cyano-4''-n-pentylterphenyl as liquid crystal materials, 0.005 parts of IRGACURE TPO (manufactured by BASF) and 0.005 parts of IRGACURE 184 (manufactured by BASF) as photopolymerization initiators, 0.003 parts of the compound represented by No. 3 in specific compound examples obtained in Example 1, 0.015 parts of LCD212 (i.e., an anthraquinone-based compound, manufactured by Nippon Kayaku Co., Ltd.), and 0.008 parts of the yellow dye compound represented by the above formula (X) at room temperature for 2 hours. With the obtained liquid crystal composition, 0.010 parts of a spacer agent ("Micropearl (registered trademark) SP220" manufactured by SEKISUI CHEMICAL CO., LTD.) having a diameter of 20 µm was mixed at room temperature. The liquid crystal composition containing the spacer agent was applied onto an ITO film of a 5-cm square PET film provided with the ITO film by an applicator to form a liquid crystal composition layer. Next, this film and another 5-cm square PET film, which was the same as described above and was provided with an ITO film, were superimposed so that the liquid crystal composition layer provided on the ITO film faced the other ITO film. Thereafter, the thus obtained laminate of the two films and the liquid crystal composition layer was set at a position where the intensity of light from an LED lamp at 365 nm was 9 mW/cm² while being maintained at 23° C. with a thermoplate, and light irradiation was performed for 1 minute to photocure the photocurable compound, thereby producing a black light control element.

INDUSTRIAL APPLICABILITY

By using the anthraquinone compound of the present invention as a dichroic dye for a liquid crystal light control element, it is possible to obtain a light control element in which light leakage at the time of light shielding is suppressed and which is excellent in contrast. The light control element obtained by the present invention can be suitably used for building materials such as windows, partitions, and doors, in-vehicle materials such as windows and sunroofs, materials for exhibits such as displays and show windows displaying characters, numbers, and the like, for example.

The invention claimed is:

1. An anthraquinone compound being a dichroic dye compound represented by the following formula (1):

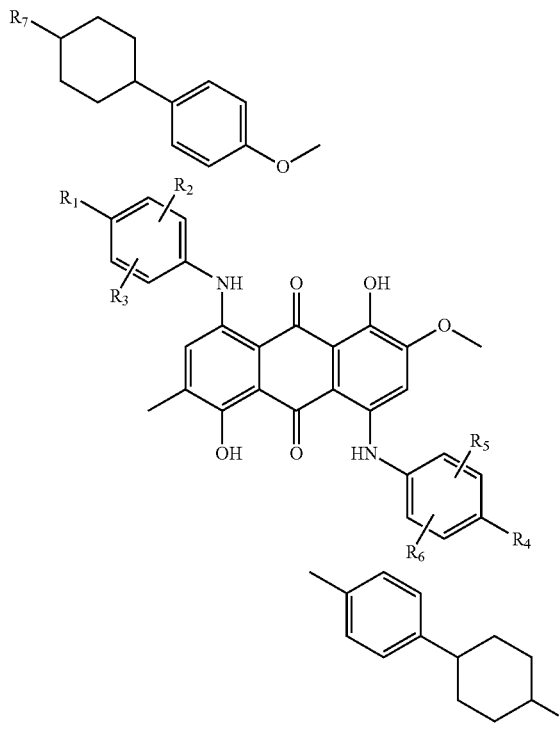

wherein $R_1$ and $R_4$ each independently represent a hydrogen atom, a C1-C12 linear alkyl group or a C3-C12 branched alkyl group, a C1-C12 linear alkoxy group or a C3-C12 branched alkoxy group, a halogen atom, $-CO_2R_9$, $-OCOR_9$, $-COR_9$, a cyano group, or a trifluoromethyl group, $R_2$, $R_3$, $R_5$, and $R_6$ each independently represent a hydrogen atom, a C1-C4 linear alkyl group or a C3-C4 branched alkyl group, a C1-C4 linear alkoxy group or a C3-C4 branched alkoxy group, a halogen atom, $-CO_2R_9$, $-OCOR_9$, $-COR_9$, a cyano group, or a trifluoromethyl group, $R_7$ and $R_8$ each independently represent a hydrogen atom or a C1-C8 linear alkyl group or a C3-C8 branched alkyl group, and $R_9$ each independently represents a C1-C12 linear alkyl group or a C3-C12 branched alkyl group, a substituent represented by the following formula (a):

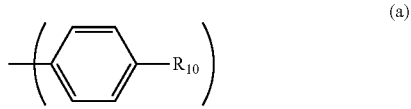

wherein $R_{10}$ represents a hydrogen atom, a C1-C8 linear alkyl group or a C3-C8 branched alkyl group, or a C1-C8 linear alkoxy group or a C3-C8 branched alkoxy group, or a substituent represented by the following formula (b):

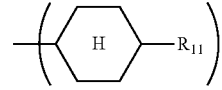

wherein $R_{11}$ represents a hydrogen atom or a C1-C8 linear alkyl group or a C3-C8 branched alkyl group.

2. The anthraquinone compound according to claim 1, wherein at least one of $R_1$ to $R_6$ is other than a hydrogen atom.

3. The anthraquinone compound according to claim 2, wherein $R_9$ is each independently a C1-C8 linear alkyl group or a C3-C8 branched alkyl group.

4. The anthraquinone compound according to claim 3, wherein $R_1$ and $R_4$ are each independently a hydrogen atom, a C1-C8 linear alkyl group or a C3-C8 branched alkyl group, a C1-C8 linear alkoxy group or a C3-C8 branched alkoxy group, a fluorine atom, a chlorine atom, $-CO_2R_9$, $-COR_9$, a cyano group, or a trifluoromethyl group, and $R_2$, $R_3$, $R_5$, and $R_6$ are each independently a hydrogen atom, a C1-C4 linear alkyl group, a C1-C4 linear alkoxy group, a fluorine atom, a chlorine atom, $-CO_2R_9$, $-COR_9$, a cyano group, or a trifluoromethyl group.

5. The anthraquinone compound according to claim 4, wherein at least one of $R_1$, $R_2$, $R_4$, and $R_5$ is a fluorine atom, a chlorine atom, $-CO_2R_9$, $-COR_9$, a cyano group, or a trifluoromethyl group.

6. The anthraquinone compound according to claim 5, wherein at least one of $R_1$, $R_2$, $R_4$, and $R_5$ is a fluorine atom, $-CO_2R_9$, or a cyano group.

7. The anthraquinone compound according to claim 4, wherein $R_3$ and $R_6$ are a hydrogen atom.

8. The anthraquinone compound according to claim 7, wherein only one of $R_1$ and $R_2$ is a hydrogen atom, and only one of $R_4$ and $R_5$ is a hydrogen atom.

9. The anthraquinone compound according to claim 7, wherein $R_2$ and $R_5$ are a hydrogen atom.

10. The anthraquinone compound according to claim 9, wherein $R_4$ is a C3-C8 linear alkyl group or a C3-C8 branched alkyl group.

11. The anthraquinone compound according to claim 4, wherein $R_7$ and $R_8$ are each independently a C3-C8 linear alkyl group.

12. The anthraquinone compound according to claim 1, wherein a maximum absorption wavelength is 650 nm or more.

13. A liquid crystal composition comprising the anthraquinone compound according to claim 1 and a liquid crystal material.

14. The liquid crystal composition according to claim 13, further comprising a photocurable compound and a photopolymerization initiator.

15. The liquid crystal composition according to claim 13, comprising a dye compound other than the anthraquinone compound represented by formula (1).

16. A photocured product of the liquid crystal composition according to claim 14.

17. A light control element comprising the liquid crystal composition according to claim 13 sandwiched between a pair of substrates disposed opposite to each other, at least one of which is a transparent substrate having a transparent electrode.

18. A light control element comprising the photocured product according to claim 16 sandwiched between a pair of substrates disposed opposite to each other, at least one of which is a transparent substrate having a transparent electrode.

19. The light control element according to claim 17, wherein both of the pair of substrates are transparent substrates having a transparent electrode.

20. The light control element according to claim 18, wherein both of the pair of substrates are transparent substrates having a transparent electrode.

* * * * *